United States Patent [19]

Boigegrain et al.

[11] Patent Number: 5,607,958

[45] Date of Patent: Mar. 4, 1997

[54] 3-AMIDOPYRAZOLE DERIVATIVES, PROCESS FOR PREPARING THESE AND PHARMACEUTICAL COMPOSITIONS CONTAINING THEM

[75] Inventors: Robert Boigegrain, Assas; Danielle Gully, Saubens; Francis Jeanjean, Valflaunes; Jean-Charles Molimard, Saint-Gely-du-Fesc, all of France

[73] Assignee: Sanofi, Paris, France

[21] Appl. No.: 394,757

[22] Filed: Feb. 27, 1995

Related U.S. Application Data

[62] Division of Ser. No. 119,830, Sep. 13, 1993, Pat. No. 5,420,141, which is a continuation of Ser. No. 747,359, Aug. 20, 1991, abandoned.

[30] Foreign Application Priority Data

Aug. 20, 1990 [FR] France ..................... 90 10486

[51] Int. Cl.$^6$ ............. A61K 31/415; C07D 231/10; C07D 231/12
[52] U.S. Cl. ............. 514/406; 548/374.1; 548/375.1; 548/377.1; 546/141; 546/153
[58] Field of Search ............. 546/141, 144, 546/153, 167; 514/307, 309, 311, 312, 314, 406; 548/374.1, 375.1, 377.1

[56] References Cited

U.S. PATENT DOCUMENTS

| | | | |
|---|---|---|---|
| 4,792,565 | 12/1988 | Shimotori et al. | 514/406 |
| 4,912,090 | 3/1990 | Yanai et al. | 514/30 |
| 4,912,109 | 3/1990 | Bagley et al. | 514/252 |
| 4,916,142 | 4/1990 | Bagley et al. | 514/318 |
| 4,950,668 | 8/1990 | Okada et al. | 514/232.2 |
| 4,954,506 | 9/1990 | Bagley et al. | 514/272 |

FOREIGN PATENT DOCUMENTS

| | | |
|---|---|---|
| 0199822 | 11/1986 | European Pat. Off. . |
| 0248594 | 12/1987 | European Pat. Off. . |
| 0365925 | 5/1990 | European Pat. Off. . |
| 89/02431 | 3/1989 | WIPO . |

*Primary Examiner*—Alan L. Rotman
*Attorney, Agent, or Firm*—Bacon & Thomas

[57] ABSTRACT

The present invention relates to new pyrazole derivatives possessing an amide group substituted with an amino acid or one of its derivatives at position 3 and variously substituted in positions 1, 2, 4 or 5 of the pyrazole ring, to a process for preparing these and to pharmaceutical compositions containing the said pyrazole derivatives as an active ingredient.

18 Claims, No Drawings

3-AMIDOPYRAZOLE DERIVATIVES, PROCESS FOR PREPARING THESE AND PHARMACEUTICAL COMPOSITIONS CONTAINING THEM

This application is a Division of application Ser. No. 08/119,830, filed Sep. 13, 1993, U.S. Pat. No. 5,420,141, which is a Continuation of application Ser. No. 07/747,359, filed Aug. 20, 1991 (now abandoned).

The present invention relates to new pyrazole derivatives possessing an amide group substituted with an amino acid or one of its derivatives at position 3 and variously substituted in positions 1, 2, 4 or 5 of the pyrazole ring, to a process for preparing these and to pharmaceutical compositions containing the said pyrazole derivatives as an active ingredient.

The compounds according to the invention possess activity with respect to the central nervous system, the cardiovascular system or the gastrointestinal system.

A large number of pyrazole derivatives are described in the literature.

1,5-Diarylpyrazoles substituted at position 3 with an alkyl chain containing from 2 to 16 carbon atoms and variously substituted, in particular with an amide, and corresponding to the formula:

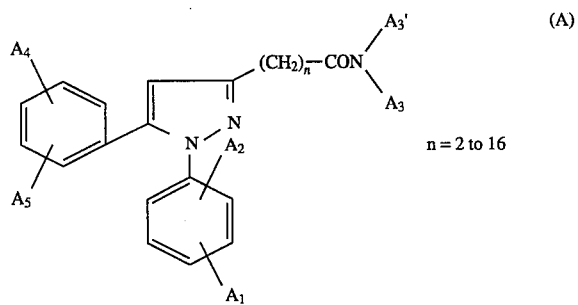

are described in European Patent 0,248,594 as possessing anti-inflammatory activity and activity with respect to the cardiovascular system.

Pyrazole derivatives of formula:

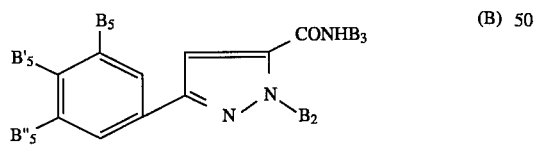

where $B_2$ represents either a hydrogen atom or a methyl group, $B_3$ represents, for example, an alkyl and $B_5$, $B'_5$ and $B''_5$ independently represent, for example, hydrogen, a halogen or a $C_1$-$C_3$ alkoxy, are described in British Patent 2,130,205 as being capable of use for the purpose of decreasing the blood uric acid level in mammals.

It is, moreover, described in Journal of the Chemical Society, 1973, 2532–2534 that 2-morpholino-5-phenyl-5-phenylazofuran salts rearrange to 1,5-diphenylpyrazoles substituted at position 3, of formula:

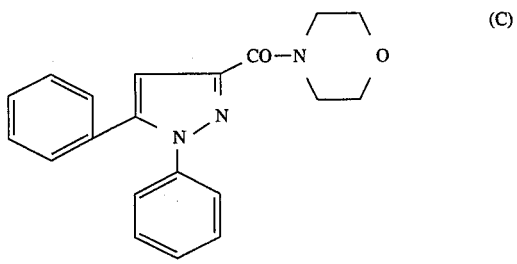

Patent Application WO 89/02,431 describes new N-containing heterocyclic, in particular pyrazolyl, compounds of formula:

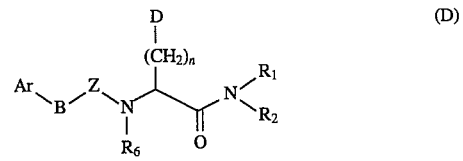

in which, for example:

Ar represents a pyrazolyl,

B represents $(CH_2)_m$ with m=0 to 4,

Z represents —C=O, n=1 to 3,

D represents $COR_3$, $R_1$ and $R_2$ represent a hydrogen or a $C_1$-$C_8$ alkyl or together go to make up a cyclic amine.

These amidopyrazole amide derivatives of acyl-glutamic or -aspartic acid are described as possessing cholecystokinin-inhibiting properties.

It has now been found that variously substituted derivatives of 3-amidopyrazole possess activity with respect to the central nervous system, and especially with respect to the neuropeptide-regulating systems, displacing, for example, tritiated or iodinated neurotensin from its receptor.

Thus, the subject of the present invention, according to one of its aspects, is a 3-amidopyrazole of formula (I) or (I'):

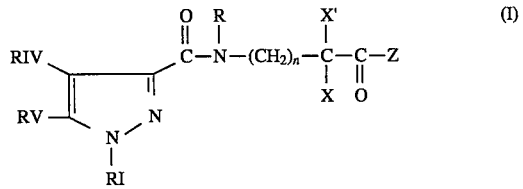

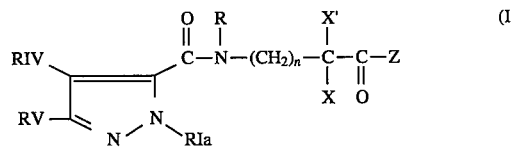

in which
$R_I$ represents:
a group

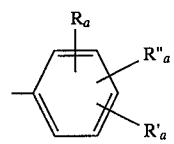

where $R_a$, $R'_a$ and $R''_a$ each independently represent a hydrogen atom, a halogen atom, a hydroxyl, a linear or branched $C_1$-$C_4$ alkyl group, a $C_1$-$C_4$ alkoxy group, a trifluoromethyl group, a trifluoromethoxy group, a nitro group, a carboxyl group or an amino group;

a carboxyalkyl or alkoxycarbonylalkyl group in which the alkyls are $C_1$–$C_4$ groups;

a cycloalkyl group in which the alkyls are $C_3$–$C_6$ groups;

a tetrahydronaphthyl group;

a pyridyl group;

a naphthyl group substituted with $R_a$, $R'_a$ and $R''_a$ as defined above;

a benzyl group substituted with $R_a$, $R'_a$ and $R''_a$ as defined above;

a cinnamyl group optionally substituted on the aromatic ring with a halogen, a hydroxyl or a $C_1$–$C_4$ alkoxy;

a quinolyl or isoquinolyl group optionally substituted with $R_a$, $R'_a$ and $R''_a$ as defined above;

a 2-benzothiazolyl group;

a quinoxalinyldione group;

a 1-phthalazinyl group;

a benzothiadiazolyl group;

a methylene group substituted with a 5- or 6-membered heterocyclic group such as, in particular, a pyridyl and a thienyl;

$R_{Ia}$ represents a benzyl group substituted with $R_a$, $R'_a$ and $R''_a$ as defined above;

R represents hydrogen or a linear or branched $C_1$–$C_4$ alkyl;

n represents 0, 1, 2 or 3;

either X represents hydrogen and X' represents hydrogen; a linear or branched $C_1$–$C_6$ alkyl; an aryl; a $C_1$–$C_4$ aminoalkyl; a $C_1$–$C_4$ hydroxyalkyl; a carboxyalkyl in which the alkyl group is a $C_1$–$C_4$ group; an acetamidoalkylcysteine in which the alkyl group is a $C_1$–$C_4$ group; a guanidinoalkyl in which the alkyl group is a $C_1$–$C_4$ group; a nitroguanidinoalkyl in which the alkyl group is a $C_1$–$C_4$ group; a $C_3$–$C_7$ cycloalkyl; an arylalkyl in which the alkyl is a $C_1$–$C_4$ group and in which the aryl is optionally substituted with a halogen or a hydroxyl or with a $C_1$–$C_3$ alkyl; a heteroarylalkyl in which the heteroaryl represents an imidazolyl or an indolyl unsubstituted or substituted with a $C_1$–$C_4$ alkyl, with a hydroxyl or with a $C_1$–$C_4$ alkoxy and in which the alkyl is a $C_1$–$C_4$ group;

or, when n is equal to zero, X represents hydrogen and X' and

—N—R considered together form a ring, unsubstituted or substituted with a hydroxyl, of formula:

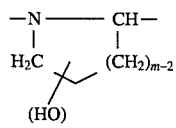

with m = 2, 3 or 4 or a ring-system of formula:

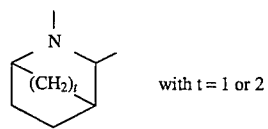

with t = 1 or 2 or a ring-system of formula:

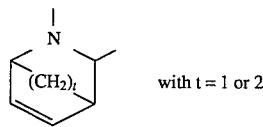

with t = 1 or 2 or an indolinyl, perhydroindole or 4,5,6,7-tetrahydrothieno[2,3-c]pyrid-6-yl ring-system;

or X and X' each independently represent a $C_1$–$C_4$ alkyl or a $C_3$–$C_6$ cycloalkyl; a phenyl;

or X and X' are linked and form together a cycloalkyl group having 2 to 12 carbon atoms, optionally substituted with a $C_1$–$C_3$ alkyl;

or X, X' and the carbon atom to which they are linked form an adamantylidene group; an adamantyl group substituted with one or two methyl groups or with a hydroxyl, a $C_1$–$C_3$ alkoxy or a halogen atom; a 1-azaadamantyl group; a quinuclidinyl group; a 4-piperidyl group optionally N-substituted with a benzyl group; a 2,2,6,6-tetramethylpiperidyl group; a tetrahydronaphthyl group; a tetrahydropyran-4-yl or tetrahydrothiopyran-4-yl group; a 2,3-dihydro-4H-benzopyran-4-yl group; a 2,3-dihydro-4H-benzothiopyran-4-yl group; a group of formula a

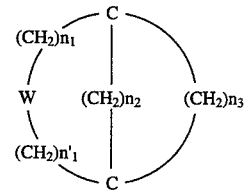

a in which $n_1$=0 or 1, $n'_1$=1 or 2, $n_2$=1, $n_3$=2 or 3 and W represents a carbon atom or an oxygen atom, this group of formula a) being attached to

and to —C(O)—Z as defined above through one carbon atom of one or other of the rings, or a group of formula b

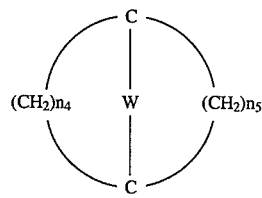

b in which $n_4$=2, 3 or 4, $n_5$=2 or 3 and W represents a carbon or oxygen atom, this group of formula b) being attached to

and to —C(O)—Z as defined above through one carbon atom of one or other of the two rings, it being possible for the rings of the above groups a and b to be optionally substituted on one and/or other of the rings with one or two $C_1$-$C_4$ alkyl groups and it not being possible for the amino acid to be at the alpha-position with respect to W when W represents oxygen; a bicyclo[2.2.1]hept-5-en-2-yl group; an 8-oxabicyclo[3.2.1]oct-6-en-3-yl group; an 8-thiabicyclo-[3.2.1]oct-3-yl group;

or X represents hydrogen and X' is an adamantyl group; an adamantyl group substituted with one or two methyls, with a hydroxyl, a $C_1$-$C_3$ alkoxy or a halogen atom; a 1-azaadamantyl group; a group of formula a or b as defined above, it not being possible for the bond between these ring-systems and the carbon carrying —COZ and —N—R to be at the alpha-position with respect to W when the latter represents oxygen;

Z represents a hydroxyl group or a $C_1$-$C_6$ alkoxy group; an oxygen atom substituted with a carboxylic acid-protecting group such as a tert-butyl, a benzyl, a benzyl substituted with a halogen atom, a $C_1$-$C_6$ alkyl, a trifluoromethyl, a trifluoromethoxy or a carboxyl group; an amino group; a nitrogen atom substituted with a carboxyalkyl in which the alkyl is a linear or branched $C_1$-$C_6$ group, with the limitation that, if Z represents a nitrogen atom substituted as defined above and if n=0, then, when X=H, X' cannot be a group:

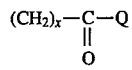

in which x=1 or 2 and Q is a hydroxyl, a free amino or amino substituted with a $C_1$-$C_6$ dialkyl or a $C_1$-$C_6$ alkoxy;

$R_{IV}$ represents a hydrogen atom, a halogen atom or a $C_1$-$C_6$ alkyl;

$R_V$ represents:

a group

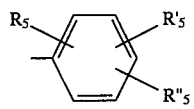

where $R_5$, $R'_5$ and $R''_5$ each independently represent a hydrogen atom, a halogen atom, a linear or branched $C_1$-$C_4$ alkyl, a hydroxyl, a $C_1$-$C_4$ alkoxy, a nitro, a trifluoromethyl, a trifluoromethoxy, a cyano, an amino, a carboxyl, a $C_1$-$C_4$ carboxyalkyl or a phenyl;

a naphthyl group unsubstituted or substituted with a $C_1$-$C_4$ alkyl;

a pyridyl group;

a styryl group unsubstituted or substituted with a $C_1$-$C_4$ alkyl;

or alternatively $R_{IV}$ and $R_V$ considered together represent:

a group

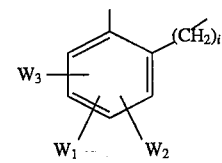

in which the phenyl group substitutes the pyrazole at position 5 and the group —$(CH_2)_i$— in which i=1 to 3 substitutes the pyrazole at position 4, $W_1$, $W_2$ and $W_3$ substitute the benzene ring and independently represent hydrogen, a halogen or a hydroxyl group;

or one of its possible salts with organic or inorganic acids or with inorganic or organic bases.

In the present description, "aryl" denotes aromatic rings such as, for example, phenyl.

When the compounds (I) or (I') include an asymmetric carbon, the enantiomers form part of the invention.

When the compounds (I) or (I') contain a group of formula a) or b), the cycloaliphatic amino acids comprise both those for which the amine function is in the endo position with respect to the aliphatic ring system and those for which the amine function is in the exo position with respect to the aliphatic ring system.

The possible salts of the products of formula (I) or (I') according to the present invention comprise both those with inorganic or organic acids which permit an appropriate crystallisation or separation of the compounds of formula (I) or (I'), such as picric acid or oxalic acid, and those which form pharmaceutically acceptable salts such as the hydrochloride, hydrobromide, sulphate, hydrogen sulphate, dihydrogen phosphate, methanesulphonate, methyl sulphate, maleate, fumarate and 2-naphthalenesulphonate.

The possible salts of the products of formula (I) or (I') also comprise the salts with cations, for example the alkali metal or alkaline earth metal salts such as the sodium, potassium and calcium salts, the sodium salt being preferred, when the said product of formula (I) or (I') contains a carboxylic acid group.

A particular class of the compounds of the invention consists of the compounds of formula (I) or (I') in which $R_I$ is either a naphthyl group or a phenyl group substituted with $R_a$, $R'_a$ and $R''_a$ as defined above, the other substituents being as defined above.

Another preferred group of the compounds of the invention consists of the compounds of formula (I) or (I') in which $R_V$ represents a naphthyl or phenyl group substituted with $R_5$, $R'_5$ and $R''_5$ as defined above, the other substituents being as defined above. Preferably, $R_5$, $R'_5$ or $R''_5$ is hydrogen or a $C_1$-$C_4$ alkoxy.

Another preferred group of the compounds of the invention consists of the compounds of formula (I) or (I') in which R,Z,n, $R_{IV}$ and $R_V$ are as above defined and X, X' and the carbon atom to which they are linked form an adamantylidene group, a group of formula a or of formula b as above defined.

According to another of its aspects, the present invention relates to a process for the preparation of the compounds of formula (I) and (I'), characterized in that a functional derivative of formula (II) or (II'):

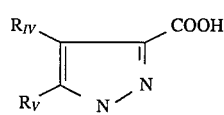

(II)

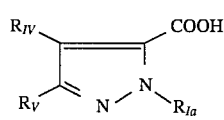

(II')

in which $R_I$, $R_{IV}$, $R_V$ and $R_{Ia}$ are as defined above, is treated with an amino acid, optionally protected by the protective The esters (IIa) and (II'a) which are precursors of the carboxylic acids (II) and (II'), defined above, are synthesised by applying the method described in Chem. Pharm. Bull, 1984, 32, 4, 1577.

The process for preparing the compounds (I) or (I') via the esters (IIa) and (II'a) is represented by the following scheme:

SCHEME 1

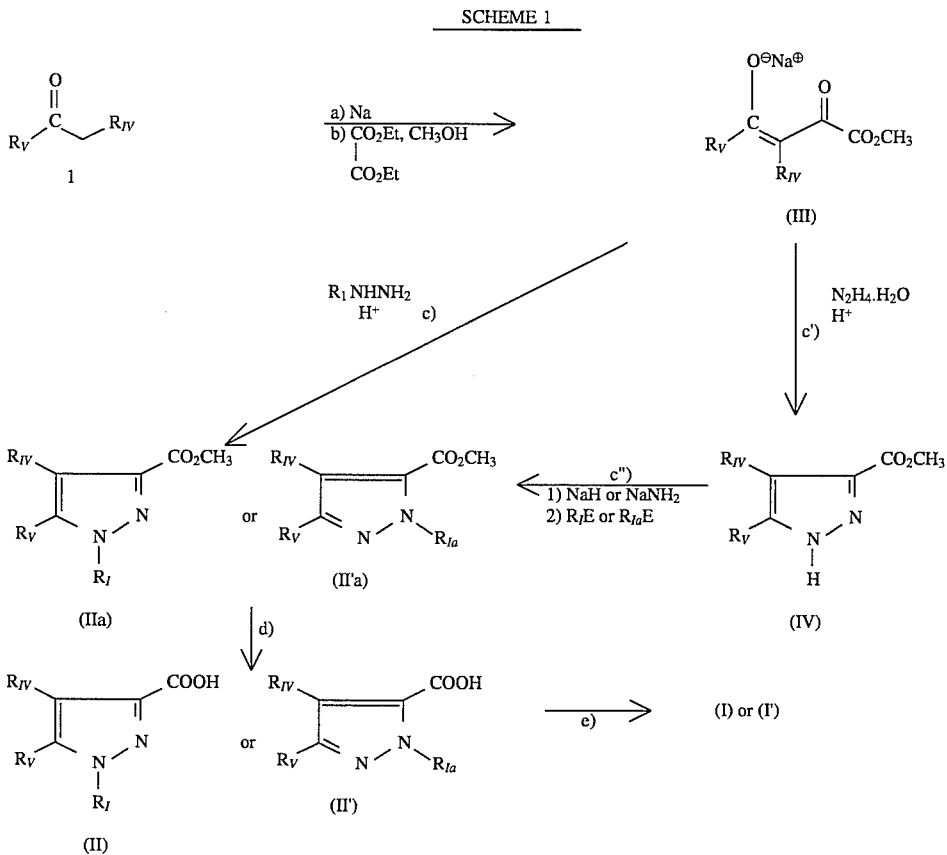

groups customary in peptide synthesis, of formula:

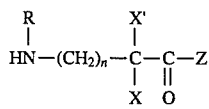

(V)

in which R, n, X, X' and Z are as defined above or optionally protected.

As a functional derivative of the pyrazolecarboxylic acid of formula (II) or (II'), it is possible to use the acid chloride, the anhydride, a mixed anhydride, an ester, an activated ester, for example the p-nitrophenyl ester, or the free acid judiciously activated, for example, with N,N-dicyclohexylcarbodiimide or with benzotriazolyl-N-oxytris(dimethylamino)phosphonium hexafluorophosphate (BOP).

The compounds (I) and (I') thus prepared may then be deprotected, where appropriate, to yield the corresponding free acids.

The first step a) consists in the preparation of the sodium enolates of a ketone of formula 1, in which $R_V$ and $R_{IV}$ are as defined above, which are reacted with an equimolar amount of ethyl oxalate (step b)) in an alkanol such as, for example, methanol, according to L. CLAISEN, Ber., 1909, 42, 59. After precipitation in ethyl ether, the sodium enolates (III) are separated by filtration.

The sodium enolates (III) thus prepared and an excess of hydrazine or of a hydrazine derivative $R_I$-NHNH$_2$ are then heated to reflux of acetic acid (step c)).

In the case where $R_I$ represents a substituted or unsubstituted benzyl group $R_{Ia}$, there is obtained, during the condensation of the benzylhydrazine with the compounds (III), a mixture, in variable proportions depending on the nature and position of the substituents of $R_V$, of the compounds (IIa) and its isomer (II'a) of formula:

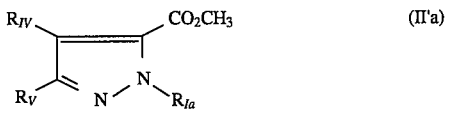

in which $R_{Ia}$, $R_{IV}$ and $R_V$ are as defined above.

The two isomers (IIa) and (II'a) may then be separated by column chromatography. On saponification of the esters, the pure isomeric acids are obtained, which acids are reacted, for example, with sulphinyl chloride. The acid chlorides are then condensed with the amino acids of formula (V) to yield the compounds (I) and (I') according to the invention (step e)).

A variant of the process, in the case where $R_I$ is a benzyl or cinnamyl group, consists in the condensation of unsubstituted hydrazine with the compound (III) (step c')) to yield the 1H-pyrazole derivative (IV), which is then substituted in the presence of NaH or NaNH$_2$ with a group $R_IE$ or $R_{Ia}E$ (stepc")), where E represents a group which can be eliminated such as a halogen, a p-toluenesulphonyloxy (tosyloxy) or a methanesulphonyloxy (mesyloxy).

The 3-amidopyrazole derivatives (I) and (I') which are subjects of the invention are then prepared from the pyrazole acids by converting the ester derivatives (IIa) and (II'a) to their corresponding acids (II) or (II') by the action of an alkaline agent such as, for example, potassium hydroxide, followed by acidification (step d), then the corresponding compounds of formula (I) and (I') are prepared as described above.

If the amino acid contains a hydroxyl group as a substituent, the latter may be protected by an O-protecting group customarily used, and then deprotected according to the usual methods.

When the product of formula (I) or (I') possesses a basic function and is obtained in the form of a free base, the salification is performed by treatment with the chosen acid in an organic solvent. On treatment of the free base, dissolved, for example in an alcohol such as isopropanol, with a solution of the chosen acid in the same solvent, the corresponding salt is obtained, which salt is isolated according to conventional techniques. Thus, for example, the hydrochloride, hydrobromide, sulphate, hydrogen sulphate, dihydrogen phosphate, methanesulphonate, methyl sulphate, oxalate, maleate, fumarate or 2-naphthalenesulphonate is prepared.

When the compound of formula (I) or (I') possesses a basic function and is isolated in the form of one of its salts, for example the hydrochloride or oxalate, the free base may be prepared by neutralisation of the said salt with an inorganic or organic base such as sodium hydroxide or triethylamine, or with an alkali metal carbonate or bicarbonate such as sodium or potassium carbonate or bicarbonate.

When the product of formula (I) or (I') contains an acid group, the compound thereby obtained may be converted to a metal salt, in particular an alkali metal salt such as the sodium salt, or an alkaline earth metal salt such as the calcium salt, according to conventional processes.

The compounds (I) or (I') according to the invention were subjected to biochemical tests.

The same compounds (I) or (I') and their salts displace, at concentrations of less than one micromolar, [Tyr$^3$-iodinated] neurotensin from its receptor on guinea pig brain membranes, according to the method described by SADOUL J. L. et al., Biochemical and Biophysical Research Communications, 1984, 120, 3, 812–819.

The compounds of the present invention are of low toxicity; in particular, their acute toxicity is compatible with their use as a medicinal product. For such a use, an effective amount of a compound of formula (I) or (I') or of one of their pharmaceutically acceptable salts is administered to mammals.

The compounds (I) or (I') according to the invention are the first potential non-peptide synthetic medicinal products capable of binding to the neurotensin receptor and capable of being useful in pathological states associated with a dysfunction of the dopaminergic systems, for example as antipsychotics (D. R. HANDRICH et al., Brain Research, 1982, 231, 216–221 and C. B. NEMEROFF, Biological Psychiatry, 1980, 15-2, 283–302), and in disorders of the cardiovascular or gastrointestinal system.

Thus, the subject of the present invention, according to another of its aspects, is pharmaceutical compositions containing as active principles the compounds of formula (I) or (I') or their possible pharmaceutically acceptable salts.

In the pharmaceutical compositions of the present invention for oral, sublingual, subcutaneous, intramuscular, intravenous, transdermal or rectal administration, the active principles may be administered, in unit dosage forms, as a mixture or with conventional pharmaceutical excipients, to animals and human beings. The appropriate unit dosage forms comprise forms for oral administration such as tablets, gelatin capsules, powders, granules and oral solutions or suspensions, forms for sublingual and buccal administration, forms for subcutaneous, intramuscular or intravenous administration and forms for rectal administration.

In order to obtain the desired effect, the dose of active principle can vary between 1 and 1,000 mg per day, and preferably between 2 and 500 mg.

Each unit dose can contain from 1 to 250 mg of active principle, and preferably from 2 to 125 mg, in combination with a pharmaceutical vehicle. This unit dose may be administered 1 to 4 times per day.

When a solid composition is prepared in the form of tablets, the active principle is mixed with a pharmaceutical vehicle such as gelatin, starch, lactose, magnesium stearate, talc, gum arabic or the like. It is possible to coat the tablets with sucrose or with other suitable substances, or they may alternatively be treated in such a way that they have a sustained or delayed activity and release a predetermined amount of active principle in continuous fashion.

A gelatin capsule preparation is obtained by mixing the active principle with a diluent and pouring the mixture obtained into soft or hard gelatin capsules.

A preparation in the form of syrup or elixir can contain the active principle together with a sweetener, preferably a zero-calorie sweetener, and methylparaben and propylparaben as antiseptic, as well as an agent imparting flavour and a suitable colouring.

The water-dispersible powders or granules can contain the active principle mixed with dispersing agents or wetting agents, or suspending agents, such as polyvinylpyrrolidone and the like, as well as with sweeteners or flavour correctors.

For rectal administration, suppositories are employed, which are prepared with binders melting at rectal temperature, for example cocoa butter or polyethylene glycols.

For parenteral administration, aqueous suspensions, isotonic saline solutions or sterile and injectable solutions are used, which contain pharmacologically compatible dispersing and/or wetting agents, for example propylene glycol or butylene glycol.

The active principle may also be formulated in the form of microcapsules, optionally with one or more excipients or additives.

The examples which follow illustrate the invention without, however, limiting it.

The instantaneous melting points (m.p.) of the crystallised products were measured on a Kofler heating stage and are expressed in degrees Celsius. In the tables which follow, the following abbreviations have been used:

| | |
|---|---|
| CH | cyclohexane |
| $CH_2Cl_2$ | dichloromethane |
| EtOH | ethanol |
| $Et_2O$ | diethyl ether |
| Hx | hexane |
| Pn | pentane |
| $iPr_2O$ | diisopropyl ether |
| iPrOH | isopropanol |
| AcOEt | ethyl acetate |
| MEOH | methanol |
| C* | means configuration of the asymmetric carbon. |

The following abbreviations are used in the NMR spectra:

| | |
|---|---|
| M | multiplet |
| S | singlet |
| BS | broad singlet |
| D | doublet |
| Har | aromatic H |
| o: ortho; m: meta | |

PREPARATION OF THE SYNTHESIS INTERMEDIATES

A. Preparation of the hydrazine derivatives ($R_I NHNH_2$)

A large number of hydrazine derivatives were commercial products.

The others were prepared according to known methods by diazotisation of the corresponding aromatic amine followed by reduction of the diazonium salt. Thus, as an example, the preparation of the following may be mentioned:

5,6,7,8-tetrahydro-1-naphthylhydrazine, according to R. FUSCO et al., Gazz. Chim. Ital., 1974, 104, 813–817;

8-hydrazinoquinoline, according to A. ALBERT et al., J. Chem. Soc., 1967, 1533–1541;

5-hydrazionquinoline and 5-hydrazinoisoquinoline, according to M. G. FERLIN et al., Il Farmaco, 1989, 44 (12), 1141–1155.

B. Preparation of the pyrazolecarboxylic acids (II)

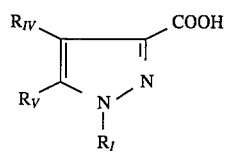

This preparation is carried out according to the above described method.

Table A below shows, as an example and without implied limitation, the characteristics of acids of formula (II).

TABLE A

| $R_I$ | $R_5$ | $R'_5$ | M.p.; °C. |
|---|---|---|---|
| tetrahydronaphthyl | $OCH_3$ | $OCH_3$ | 202 |
| naphthyl | $CH_3$ | $CH_3$ | >260 |
| naphthyl | $OCH_3$ | $OCH_3$ | 211 |
| naphthyl | $OC_2H_5$ | $OC_2H_5$ | 262 |
| 4-chloronaphthyl | $OCH_3$ | $OCH_3$ | 220 |
| quinolinyl | $OCH_3$ | $OCH_3$ | 241 |
| chloroquinolinyl | $OCH_3$ | $OCH_3$ | >260 |
| isoquinolinyl | $OCH_3$ | $OCH_3$ | >260 (decomposition) |

C. Preparation of the amino acids

The non-commercial products are prepared according to the STRECKER synthesis (Ann., 75, 27, 1850) or according to the synthesis of H. T. BUCHERER et al., J. Pract. Chem., 1934, 141, 5, followed by a hydrolysis to yield the amino acids; for example, 2-amino-2-adamantanecarboxylic acid is prepared according to H. T. NASANTA et al , J. Med. Chem., 1973, 16 (7), 823.

α-Aminocycloalkanecarboxylic acids are prepared according to J. W. TSANG et al., J. Med. Chem, 1984, 27, 1663.

(R)- and (S)-Cyclopentylglycines are prepared by resolution of benzyloxycarbonylcyclopentylglycine.

1) Preparation of racemic benzyloxycarbonylcyclopentylglycine

This compound is prepared by the following reaction scheme 2.

SCHEME 2

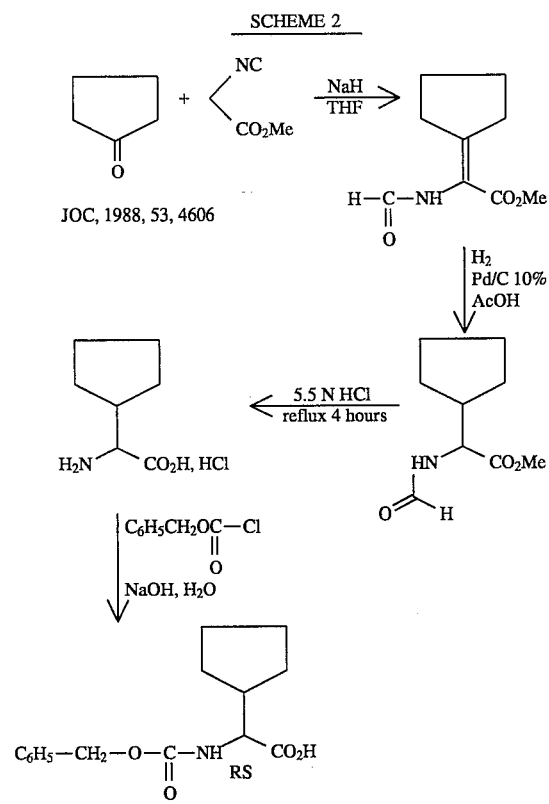

2) (RS)-Cyclopentylglycine hydrochloride

80% NaH (1.8 g) is dissolved in anhydrous THF (50 ml). A mixture of cyclopentanone (4.2 g) and methyl isocyanoacetate (5 g) in THF (50 ml) is added dropwise and with stirring. When the addition is complete, the mixture is left for 2 hours. It is cooled to 5° C. and acetic acid in 10% aqueous solution (50 ml) is added slowly. The THF is evaporated off under vacuum. The aqueous residue is extracted with chloroform (3×120 ml). The organic phase is dried over $Na_2SO_4$ and concentrated under vacuum.

The residue is taken up with pentane, filtered off and washed with pentane.

The solid (7.6 g) is dissolved in acetic acid (100 ml). Palladium on charcoal (10% Pd) (3 g) is added and the mixture is stirred at atmospheric pressure and room temperature under hydrogen for 24 hours (1 liter of hydrogen is absorbed). The mixture is filtered through Celite, which is washed several times with acetic acid. The filtrate is evaporated under vacuum. The residue is taken up in 5.5N hydrochloric acid (70 ml). The mixture is heated to reflux for 4 hours. It is concentrated to dryness, and the residue is treated azeotropically with toluene several times and dried under vacuum. The expected product is obtained.

m=7.2 g.

NMR $D_2O$: 8 H at 1.6 (M, ring $CH_2$); 1 H at 2.20 (M, ring CH); 1 H at 3.80 (D,J=7 $CHCO_2H$); 3 H at 8.60 (BS, $NH_3^+$).

3) Acylation with benzyl chloroformate (RS)-Cyclopentylglycine hydrochloride (7.2 g) is dissolved in 2N sodium hydroxide solution (65 ml). Benzyl chloroformate (8.5 g) in THF (30 ml) is added dropwise, cooling to 5° C. The mixture is left stirring overnight at room temperature. It is acidified with concentrated HCl to pH 2 (T≦5° C.). It is extracted with chloroform and the organic phase is dried and evaporated. The residue is taken up with pentane. (RS)-Benzyloxycarbonylcyclopentylglycine is obtained.

M.p. 110° C.

4) Resolution of benzyloxycarbonylcyclopentylglycine

Benzyloxycarbonylcyclopentylglycine (5.54 g) is dissolved in absolute ethanol (65 ml). (–)-(1R,2S,)-1,2-Diphenyl-1-ethanol-2-amine, prepared according to J. WEIJLARD et al., J. Am. Chem. Soc. 1951, 73, 1216, is added. The mixture is heated to dissolution. It is left to precipitate overnight and is filtered. 2.8 g of the salt (m.p. 175° C.) are obtained. The mother liquors are kept.

The salt obtained is taken up with water (20 ml), HCl (30 ml) and ether (100 ml). The mixture is stirred to dissolution. The organic phase is separated after settling has taken place, dried and evaporated. Benzyloxycarbonylcyclopentylglycine is obtained, which is treated immediately with concentrated HCl (15 ml) and AcOH (15 ml). The mixture is heated to reflux for 3 hours. It is evaporated to dryness. The residue is taken up with dry ether, filtered off and dried. (S)-Cyclopentylglycine hydrochloride is obtained.

$[\alpha]_D^{25}=+10.4°$ (c=0.5, N HCl).

m=0.6 g.

The mother liquors are evaporated to dryness and the residue is taken up with $H_2O$ (50 ml), HCl (60 ml) and $Et_2O$ (300 ml). The mixture is stirred and everything is dissolved. The ether phase is separated after settling has taken place, dried and evaporated. The benzyloxycarbonylcyclopentylglycine (4.3 g) is recovered and is placed in absolute ethanol (50 ml) with (+)-(1S,2R)-1,2-diphenyl-1-ethanol-2-amine (3.30 g). The mixture is heated to dissolution, left standing overnight and filtered. 4.15 g of salt are obtained.

M.p. 175° C.

This salt is taken up with water (20 ml), N HCl (40 ml) and ether (200 ml). The mixture is stirred. The ether phase is dried and evaporated and the residue is then treated with concentrated HCl (10 ml) and acetic acid (100 ml). The mixture is heated to reflux for 3 hours and concentrated under vacuum and the residue is taken up with anhydrous ether to obtain (R)-cyclopentylglycine hydrochloride.

m=1.2 g.

$[\alpha]_D^{25}=-10.5$ (c=0.85, N HCl).

Optical purity of the (R)-cyclopentylglycine:

0.10 g of the above hydrochloride are dissolved in absolute methanol. The mixture is cooled to –40° C., 0.5 ml of thionyl chloride is added and the mixture is left for 24 hours at room temperature. It is concentrated under vacuum, the residue is taken up in anhydrous chloroform (20 ml), and triethylamine (0.2 ml) and (S)-phenylmethyl isocyanate (0.074 ml) are added. The mixture is left for 24 hours and the chloroform is then evaporated off. The residue is chromatographed on silica gel; eluent: ethyl acetate. Concentration of the pure fractions yields 0.1 g of the methyl ester. The NMR spectrum in $CDCl_3$ shows, at around 3.8 ppm, the presence of two signals for —$CO_2CH_3$. Integration shows that the weaker signal represents 4%, the more intense signal 96%. The enantiomeric excess is hence 92%.

It is also possible to prepare the cycloalkyl-α-amino acids of R or S configuration by stereospecific enzymatic hydrolysis of the corresponding racemic N-acetyl derivatives, according to J. HILL et al., J. Org. Chem., 1965, 1321.

EXAMPLE 1

(S)-2-{[1-Phenyl-5-(4-pyridyl)-3-pyrazolyl]carbonylamino}-4-methylpentanoic acid methyl ester (I): R=H; n=0; X'=H; X=—CH$_2$—CH—(CH$_3$)$_2$; Z=OCH$_3$; R$_I$=C$_6$H$_5$; R$_{IV}$=H;

R$_V$= 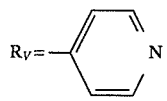

0.35 g of 1-phenyl-5-(4-pyridyl)-3-pyrazolecarboxylic acid is dissolved in 5 ml of dimethylformamide in the presence of 0.45 ml of diisopropylethylamie (DIPEA) and 0.59 g of benzotriazolyl-N-oxytris(dimethylamino)phosphonium hexafluorophosphate (BOP). 0.23 g (1 equivalent) of (S)-leucine methyl ester hydrochloride, dissolved in 0.4 ml of DIPEA, is then added and the reaction mixture is left overnight at room temperature. The solvents are concentrated under vacuum, the residual oil is extracted with dichloromethane and this solution is washed with water, then with sodium bicarbonate solution and again with water. The organic phase is dried over sodium sulphate and then concentrated under vacuum. The residue is chromatographed on silica gel; eluent: ethyl acetate.

m=0.18 g.

$^1$H NMR spectrum of the compound 1: 3H at 8.82 (M, Har o to N and CONH); 5H at 7.50 (M, Phe Har); 3H at 7.27 (Har m to N and pyrazole H$_4$); 1H at 4.60 (M, α-Leu H); 3H at 3.77 (S, CO$_2$CH$_3$); 1H at 2.00 (M, γ-Leu H); 2H at 1.70 (M, β-Leu H); 6H at 1.00 (2D, Leu CH$_3$).

EXAMPLE 2

(S)-2-{[1-Phenyl-5-(2-naphthyl)-3-pyrazolyl]carbonylamino}-3-phenylpropanoic acid (I): R=H; n=0; X'=H; X=—CH$_2$—C$_6$H$_5$; Z=OH; R$_I$=C$_6$H$_5$; R$_{IV}$=H;

R$_V$= 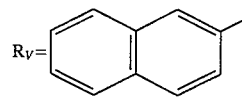

Preparation of 5-(2-naphthyl)-1-phenyl-3-pyrazolecarbonyl chloride 5 g of 5-(2-naphthyl)-1-phenyl-3-pyrazolecarboxylic acid are dissolved in 56 ml of toluene, and 3.5 ml of sulphinyl chloride are added dropwise to this solution. The mixture is heated to 90° for 2½ h, then concentrated under vacuum. The residual oil is taken up twice in toluene and concentrated under vacuum.

m=5 g.

Preparation of the compound 2

4.9 g of (S)-phenylalanine are added to 60 ml of 2N sodium hydroxide solution, and a solution of 4 g of the acid chloride prepared above, dissolved in 65 ml of tetrahydrofuran, is then added dropwise. The reaction mixture is left overnight at room temperature and then concentrated under vacuum. The residue is taken up in water and the pH is adjusted to 1 by adding hydrochloric acid. The solution is extracted with dichloromethane and the organic phase is washed with water and with saturated sodium chloride solution, dried over sodium sulphate, filtered and concentrated under vacuum. The residue is recrystallised from pentane.

m=2 g.

M.p. 226° C.

EXAMPLE 3

(S)-N,N-Diethyl-2-{[1-phenyl-5-(2-naphthyl)-3-pyrazolyl]carbonylamino}-3-phenylpropanamide (I): R=H; n=0; X'=H; X=—CH$_2$—C$_6$H$_5$; Z=—N—(C$_2$H$_5$)$_2$; R$_1$=C$_6$H$_5$; R$_{IV}$=H;

R$_V$= 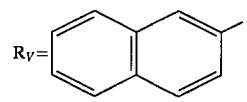

2 g of the product obtained according to Example 2, 0.88 g of dicyclohexylcarbodiimide (DCCI) and 1.14 g of 1-hydroxybenzotriazole (HOBT) are dissolved in 68 ml of tetrahydrofuran and the mixture is stirred for ¾ hour at room temperature. 0.4 g of diethylamine is then added and the reaction mixture is left at room temperature for 24 hours.

The dicyclohexylurea is separated by filtration and the mother liquors are concentrated under vacuum. The residue is chromatographed on silica gel; eluent: ethyl acetate. The fractions of pure product are concentrated under vacuum and the residue is recrystallised from pentane.

m=1.46 g

M.p. 70° C.

EXAMPLE 4

(S)-2-{(1-Phenyl-4,5-dihydrobenz[g]indazol-3-yl)carbonylamino}-4-methylpentanoic acid (I):

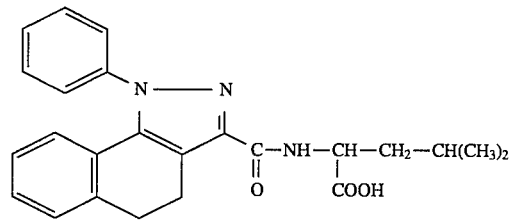

A) β-Ketocarbethoxy-α-tetralone sodium salt

This intermediate is prepared according to the method described by D. RAMESH et al. Indian Journal of Chemistry, 1989, 28B, 76–78.

B) 1-Phenyl-4,5-dihydrobenz[g]indazole-3-carboxylic acid ethyl ester 8.04 g of the sodium salt obtained above are dissolved in 100 ml of acetic acid. 3.3 ml of phenylhydrazine are added and the reaction mixture is heated to reflux for 8 hours. The cooled mixture is poured into ice-cold water; a precipitate is separated by filtration and washed with water and then with pentane.

m=10.5 g.

C) 1-Phenyl-4,5-dihydrobenz[g]indazole-3-carboxylic acid 9.5 g of the product obtained above are dissolved in 100 ml of methanol and 100 ml of water. 4.2 g of potassium hydroxide are added and the reaction mixture is heated to reflux for 5 hours. The mixture is poured into ice-cold water and the resulting mixture is then washed with ethyl acetate. The aqueous phase is acidified to pH 2 by adding hydrochloric acid, and a precipitate is separated by filtration and washed with water and then with pentane.

m=7.3 g.

D) 1-Phenyl-4,5-dihydrobenz[g]indazole-3-carbonyl chloride 2.8 g of the acid obtained above are dissolved in 100 ml of toluene, 2.2 ml of sulphinyl chloride are then added and the mixture is heated to 100° C. for 5 hours. The solution is concentrated under vacuum, 20 ml of toluene are added and the mixture is concentrated under vacuum. The same operation is repeated twice.

E) Compound 4

0.88 g of (S)-leucine is dissolved in a solution of 1.33 g of sodium hydroxide in 20 ml of water. This solution is cooled, 0.99 g of the acid chloride prepared above, dissolved in 16 ml of tetrahydrofuran, is then added and the reaction mixture is left stirring at room temperature for 18 hours. The solution is concentrated under vaccum, and the residue is taken up in ice and acidified to pH 2 by adding hydrochloric acid and then extracted with ethyl acetate. The organic phase is dried over sodium sulphate, filtered and concentrated under vacuum. The residue is recrystallised from isopropyl ether.

m=1 g.
M.p. 100° C.

EXAMPLE 5

(S)-2-{[1-Benzyl-3-(2-naphthyl)-5-pyrazolyl]carbonylamino}-3-phenylpropanoic acid (I'): R=H; n=0; X'=H; X=—CH$_2$—C$_6$H$_5$; Z=OH; R$_{Ia}$=—CH$_2$—C$_6$H$_5$; R$_{IV}$=H;

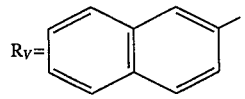

A) The reaction of methyl 2-naphthoylpyruvate with benzylhydrazine hydrochloride yields a mixture of the following esters: 1-benzyl-5-(2-naphthyl)-3-(pyrazolecarboxylic acid methyl ester and 1-benzyl-3-(2-naphthyl)-5-pyrazolecarboxylic acid methyl ester.

Chromatography on silica gel enables the two isomers to be separated. 1-Benzyl-5-(2-naphthyl)-3-pyrazolecarboxylic acid methyl ester is eluted first with a 50:50 (v/v) ethyl acetate/hexane mixture. 1-Benzyl-3-(2-naphthyl)-5-pyrazolecarboxylic acid methyl ester is eluted as a second fraction.

B) 1-Benzyl-3-(2-naphthyl)-5-pyrazolecarboxylic acid

The acid was prepared by saponification of the ester obtained above.

C) 1-Benzyl-3-(2-naphthyl)-5-pyrazolecarbonyl chloride

The acid chloride is prepared by the action of sulphinyl chloride on the above acid, and is not isolated.

D) Compound 5

0.28 g of (S)-phenylalanine are dissolved in a cooled sodium hydroxide solution. A solution of 0.3 g of the acid chloride prepared above in 5 ml of THF is then added and the reaction mixture is left at room temperature for 24 hours. The THF is concentrated under vacuum, and the residue is taken up in water and neutralised by adding concentrated hydrochloric acid. The product is extracted with ethyl acetate and the organic phase is dried over sodium sulphate and concentrated under vacuum. The residue is recrystallised from cyclohexane.

m=1 g.
M.p. 100° C.

EXAMPLE 6

(S)-2-{[1-(4'-Methoxycinnamyl)-5-(4-pyridyl)-3-pyrazolyl]carbonylamino}-4-methylpentanoic acid methyl ester (I): R=H; n=0; X'=H; X=—CH$_2$—CH—(CH$_3$)$_2$; Z=OCH$_3$;

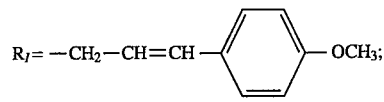

R$_{IV}$=H;

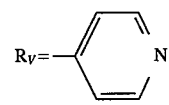

A) 1-(4'-Methoxycinnamyl)-5-(4-pyridyl)-3-pyrazolecarboxylic acid methyl ester 4.6 g of 5-(4-pyridyl)-1H-pyrazole-3-carboxylic acid methyl ester are dissolved in 60 ml of dimethylformamide, 0.63 g of sodium hydride in 80% suspension in oil is then added and the reaction mixture is heated to 40° C. for 1 hour. A solution of 5.2 g of 4'-methoxycinnamyl bromide, dissolved in 60 ml of dimethylfor-mamide, is then added to the cooled mixture and the reaction mixture is left at room temperature for 12 hours. The dimethylformamide is concentrated under vacuum, the residue is taken up in water and extracted with ethyl acetate and the organic phase is dried over sodium sulphate, filtered and concentrated under vacuum. The residual oil is chromatographed on silica gel; eluent: 50:50 (v/v) ethyl acetate/cyclohexane. The fractions of pure product are concentrated under vacuum.

m=2.6 g.
M.p. 118° C.

B) Compound 6

0.4 g of the acid obtained above is dissolved in 12 ml of dimethylformamide in the presence of 0.63 ml of DIPEA and 0.53 g of BOP. 0.22 g of (S)-leucine methyl ester hydrochloride, dissolved in 0.63 ml of DIPEA, is then added and the reaction mixture is left overnight at room temperature. The dimethylformamide is concentrated under vacuum and the residue is taken up in water. The product is extracted with ethyl acetate and the organic phase is dried over sodium sulphate, filtered and concentrated under vacuum. The residue is solidified in diisopropyl ether.

m=0.15 g.
M.p. 172° C.

EXAMPLE 7

(S)-2-{3-[1-(4'-Methoxycinnamyl)-5-(4-pyridyl)-3-pyrazolyl]carbonylamino}-3-phenylpropanoic acid sodium salt (I): R=H; n=0; X'=H; X=—CH$_2$—C$_6$H$_5$; Z=O$^-$ Na$^+$

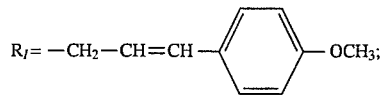

R$_{IV}$=H;

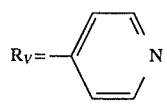

Using the procedure described in Example 6, and replacing (S)-leucine methyl ester hydrochloride by (S)-phenylalanine methyl ester hydrochloride, the methyl ester is obtained, which ester is hydrolysed to a sodium salt with 0.9 equivalent of sodium hydroxide in 10 ml of 96° strength ethanol. The mixture is left overnight at room temperature and concentrated under vacuum and the residue is washed with ether. After filtration, the compound 7 is obtained.
M.p. 137° C.

EXAMPLE 8

2-{[1-(5-Isoquinolyl)-5-(2,6-dimethoxyphenyl)-3-pyrazolyl]carbonylamino}-2-adamantanecarboxylic acid (I): R=H; n=0;

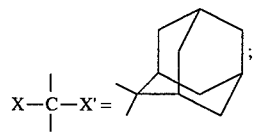

Z=OH;

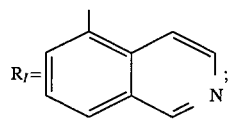

R$_{IV}$=H;

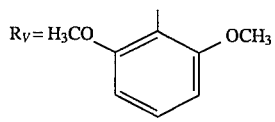

0.75 g of 2-amino-2-adamantanecarboxylic acid is dissolved in 20 ml of pyridine. 1.4 g of 1-(5-isoquinolyl)-5-(2,6-dimethoxyphenyl)-3-pyrazolecarbonyl chloride, dissolved in 20 ml of dichloromethane, are added and the reaction mixture is left overnight at room temperature. It is concentrated under vacuum, the residue is taken up with pH 2 buffer, the mixture is stirred and the precipitate is filtered off and rinsed with diisopropyl ether.
m=0.4 g.
M.p.>260° C.

EXAMPLE 9

2-{[1-(5-Quinolyl)-5-(2,6-dimethoxyphenyl)-3-pyrazolyl]carbonylamino}-2-adamantanecarboxylic acid (I): R=H; n=0;

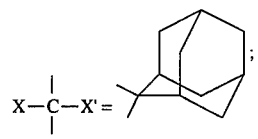

Z=OH

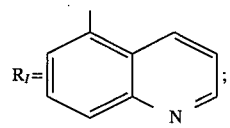

R$_{IV}$=H;

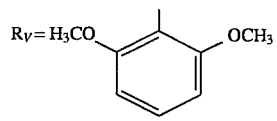

0.23 g of 2-amino-2-adamantanecarboxylic acid, 0.5 g of 1-(5-quinolyl)-5-(2,6-dimethoxyphenyl)-3-pyrazolecarbonyl chloride and 0.7 g of potassium hydroxide are dissolved in 25 ml of dichloromethane in the presence of 0.1 g of Aliquat 336®.

The reaction mixture is stirred overnight at room temperature, 0.7 g of potassium hydroxide is added and the mixture is stirred for 4 hours. It is filtered and 0.2 g of the expected product is obtained.
M.p.>260° C.

EXAMPLE 10

(S)-2-{[1-(4-Chloro-1-naphthyl)-5-(2,6-dihydroxyphenyl)-3-pyrazolyl]carbonylamino}hexanoic acid (I): R=H; n=0; X'=H; X=(CH$_2$)$_3$—CH$_3$
Z=OH;

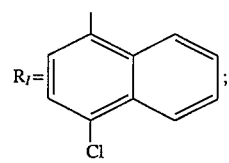

$R_{IV}$=H;

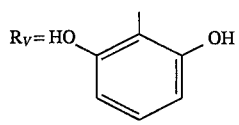

0.3 g of 2-{[1-(4-chloro-1-naphthyl)-5-(2,6-dimethoxyphenyl)-3-pyrazolyl]carbonylamino}hexanoic acid is dissolved in 6.7 ml of dichloromethane and the mixture is cooled to −70° C. 5.7 ml of boron tribromide, dissolved in 20 ml of dichlormethane, are added dropwise and the reaction mixture is left for 2 hours at −70° C. It is allowed to return to room temperature, and 12 ml of water are then added while cooling. Concentrated NaOH is added to pH 14. The aqueous phase is washed with ether and brought to pH 2, the product is extracted with ethyl acetate and the organic phase is dried over sodium sulphate, filtered and evaporated. The residue is crystallised from diisopropyl ether.

m=0.13 g.
M.p.>260° C.

EXAMPLE 11

2-{[1-(1-Naphthyl)-5-(2,6-dimethoxyphenyl)-3-pyrazolyl]carbonylamino}-2 -adamantanecarboxylic acid (I): R=H; n=0:

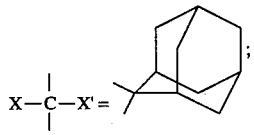

Z=OH;

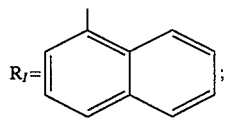

$R_{IV}$=H;

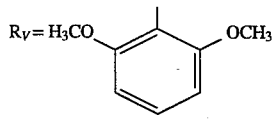

0.107 g of sodium hydroxide in 1.36 ml of water and 0.51 ml of tetrahydrofuran are cooled to 0° C. 0.52 g of 2-amino-2-adamantanecarboxylic acid is added in a single portion, and 0.53 g of 1-(1-naphthyl)-5-(2,6-dimethoxyphenyl)-3-pyrazolecarbonyl chloride, dissolved in 3 ml of tetrahydrofuran, is then added dropwise. The mixture is left for 10 minutes, and the same amount of the above acid chloride, in 3 ml of tetrahydrofuran, is added again; simultaneously, 1.32 ml of 2N sodium hydroxide are added. The reaction mixture is left for 4 days at room temperature; successively, ice-cold water is added and concentrated hydrochloric acid is added to pH 1, and the precipitate is filtered off. The crystals are washed with diisopropyl ether.

m=0.48 g.
M.p.>260° C.

EXAMPLE 12

Methyl 2-{[1-(1-naphthyl)-5-(2,6-dimethoxyphenyl)-3-pyrazolyl]carbonylamine}-2-adamantanecarboxylate (I): R=H; n=0;

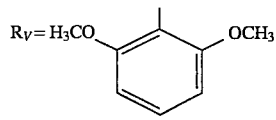

Z=OCH$_3$;

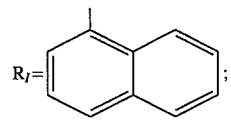

$R_{IV}$=H;

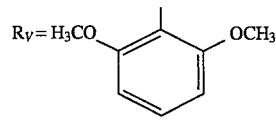

0.5 g of the compound prepared in Example 11 is dissolved in 34.6 ml of anhydrous tetrahydrofuran and 4 ml of dimethylformamide. 3.5 ml of water and 0.208 g of caesium carbonate are added and the reaction mixture is left at room temperature for 1 hour. It is concentrated under vacuum and treated azeotropically with toluene. The residue is taken up in 5 ml of tetrahydrofuran. 0.6 ml of methyl iodide is added and the reaction mixture is left for 1 hour at room temperature. It is concentrated under vacuum, the residue is taken up in water, the mixture is stirred and the precipitate is separated by filtration. The precipitate is washed with water and with pentane.

m=0.38 g.
M.p. 242°–244° C.

EXAMPLE 13

2-{[1-(7-Chloro-4-quinolyl)-5-(2,6-dimethoxyphenyl)-3-pyrazolyl]carbonylamino}-2-adamantanecarboxylic acid (I): R=H; n=0;

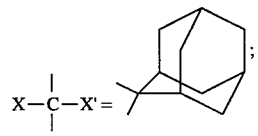

Z=OH;

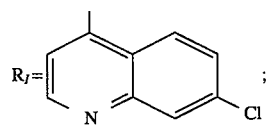

$R_{IV}$=H;

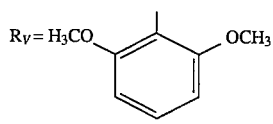

Using the procedure employed in Example 8, and replacing the acid chloride by 1-(7-chloro-4-quinolyl)-5-(2,6-dimethoxyphenyl)-3-pyrazolecarbonyl chloride, the intermediate compound of formula:

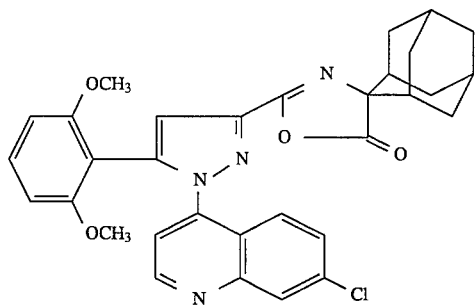

is obtained, the melting point of which is 249° C. 0.1 g of this intermediate is dissolved in 5 ml of dichlormethane; 5 ml of trifluoroacetic acid are added and the mixture is left for half an hour at room temperature. It is concentrated under vacuum to obtain the expected compound.

m=0.080 g.

M.p.>260° C.

By repeating any one of the procedures described in Examples 1 to 13, the compounds shown in Tables 1 to 15 below were prepared. In these tables, $R_3$, when it is used, represents the group:

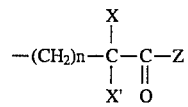

TABLE 1

| Example n° | -N(R)(R₃) | C* | M.p.; °C. crystallisation solvent |
|---|---|---|---|
| 14 | —NH—CH₂—CO₂H | — | 170 iPr₂O |
| 15 | —NH—CH₂—CO₂Et | — | 116 iPr₂O |
| 16 | —NH—(CH₂)₂—CO₂H | — | 170 iPr₂O |
| 17 | CH₃—(CH₂)₃—CH(—NH)—CO₂H | S | 70 CH |
| 18 | (CH₃)₂—CH—CH(—NH)—CO₂H | S | 152 iPr₂O |
| 19 | C₆H₅—CH₂—CH(—NH)—CO₂H | S | 214 iPr₂O |
| 20 | C₆H₅—(CH₂)₂—CH(—NH)—CO₂H | S | 79 CH |
| 21 | HO—CH₂—CH(—NH)—CO₂H | S | 242 iPr₂O |
| 22 | NH₂—(CH₂)₄—CH(—NH)—CO₂H | S | 150 iPr₂O (HCl) |

TABLE 1-continued

[Structure: 1,5-diphenyl-pyrazole-3-carboxamide with -CON(R)(R₃)]

| Example n° | -N(R)(R₃) | C* | M.p.; °C. crystallisation solvent |
|---|---|---|---|
| 23 | HN=C(NH₂)-NH-(CH₂)₃-CH(-NH-)-CO₂H | S | 125 CH (HCl) |
| 24 | HO₂C-(CH₂)₂-CH(-NH-)-CO₂H | S | 100 iPr₂O |
| 25 | N-pyrrolidine-2-CO₂H (proline) | S | 212 iPr₂O |
| 26 | indol-3-yl-CH₂-CH(-NH-)-CO₂H (tryptophan) | S | 207 iPr₂O |
| 27 | imidazol-4-yl-CH₂-CH(-NH-)-CO₂CH₃ | S | 90 iPr₂O |
| 28 | imidazol-4-yl-CH₂-CH(-NH-)-CO₂H | S | 220 EtOH,H₂O |
| 29 | cyclopentyl-CH(-NH-)-CO₂H | R S | 84 Pn,Et₂O |

TABLE 2

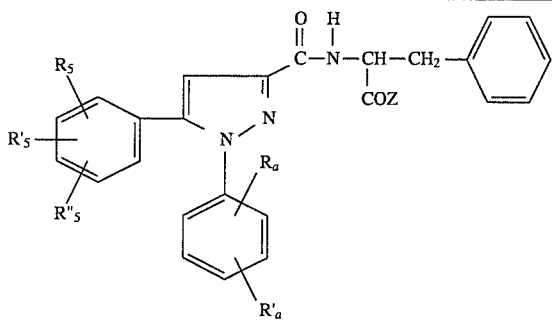

| Example No. | $R_a$ | $R'_a$ | $R_5$ | $R'_5$ | $R''_5$ | Z | M.p.; °C. crystal. solvent |
|---|---|---|---|---|---|---|---|
| 30 | H | H | 4-$CH_3$ | H | H | ONa | 140 EtOH |
| 31 | H | H | 4-$NO_2$ | H | H | $OCH_3$ | 69 Hx |
| 32 | H | H | 4-$C_6H_5$ | H | H | OH | 104 $iPr_2O$ |
| 33 | H | H | 2-Cl | 4-Cl | H | OH | 108 $iPr_2O$ |
| 34 | H | H | 2-$CH_3$ | 4-$CH_3$ | 6-$CH_3$ | OH | 120 $iPr_2O$ |
| 35 | H | H | 2-$OCH_3$ | 6-$OCH_3$ | H | OH | 99 $iPr_2O$ |
| 36 | 4-F | H | 2-F | H | H | OH | 203 $iPr_2O$ |
| 37 | 4-F | H | 4-Cl | H | H | OH | 90 Pn |
| 38 | 4-F | H | 2-$CH_3$ | H | H | OH | 208 $iPr_2O$ |
| 39 | 4-F | H | 4-$OCH_3$ | H | H | OH | 92 $iPr_2O$ |
| 40 | 4-Cl | H | 4-Cl | H | H | OH | 98 Pn |
| 41 | 4-$CH_3$ | H | 4-$OCH_3$ | H | H | OH | 94 $iPr_2O$ |
| 42 | 4-$OCH_3$ | H | 4-Cl | H | H | OH | 84 Pn |
| 43 | 4-$OCF_3$ | H | 2-F | H | H | OH | 86 $iPr_2O$ |
| 44 | 2-Cl | 4-Cl | 4-Cl | H | H | OH | 110 Pn |
| 45 | 2-Cl | 5-Cl | 4-$CH_3$ | H | H | OH | 90 Pn |
| 46 | 2-$CH_3$ | 5-F | 2-Cl | H | H | OH | 100 Pn |
| 47 | 3-Cl | 4-Cl | H | H | H | OH | 83 Hx |
| 48 | 3-Cl | 4-Cl | 4-$CH_3$ | H | H | OH | 100 Pn |
| 49 | 4-t-Bu | H | H | H | H | OH | 88 CH |
| 50 | 4-$NO_2$ | H | H | H | H | $OCH_3$ | 69 Hx |
| 51 | 4-$NH_2$ | H | H | H | H | $OCH_3$ | 97 Hx |
| 52 | 4-$NH_2$ | H | H | H | H | ONa | 155 $H_2O$ |

The compounds of Table 2 are all of S configuration.

TABLE 3

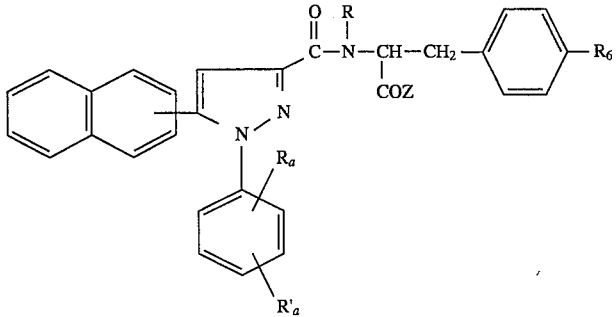

| Example No. | $R_a$ | $R'_a$ | R | Z | $R_6$ | Naphthyl position | C* | M.p; °C. crystal. solvent |
|---|---|---|---|---|---|---|---|---|
| 53 | H | H | H | OH | H | 1 | S | 221 iPr$_2$O |
| 54 | H | H | H | OH | H | 2 | R | 224 iPr$_2$O |
| 55 | H | H | CH$_3$ | OH | H | 2 | S | 84 Hx |
| 56 | H | H | H | OH | Cl | 1 | R S | 212 iPr$_2$O |
| 57 | H | H | H | OH | Cl | 2 | R S | 196 iPr$_2$O |
| 58 | H | H | H | OH | OH | 2 | S | 96 Hx |
| 59 | H | H | H | OCH$_3$ | H | 2 | S | 69 Pn |
| 60 | 2-Cl | 5-Cl | H | OH | H | 1 | S | 115 Hx |
| 61 | 2-Cl | 5-Cl | H | OH | H | 2 | S | 105 Hx |
| 62 | 2-Cl | 5-Cl | H | OH | Cl | 1 | R S | 139 Hx |
| 63 | 2-Cl | 5-Cl | H | OH | Cl | 2 | R S | 221 iPr$_2$O |
| 64 | 3-Cl | 4-Cl | H | OH | H | 1 | S | 224 iPr$_2$O |
| 65 | 3-Cl | 4-Cl | H | ONa | H | 2 | S | 140 EtOH |

TABLE 4

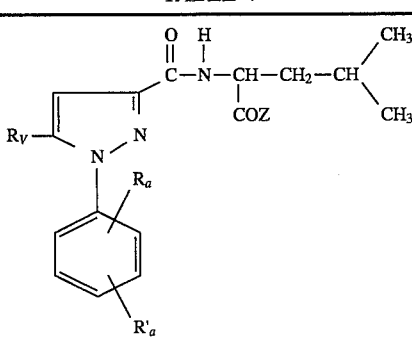

| Example No. | $R_a$ | $R'_a$ | Z | $R_V$ | C* | M.p.; °C. crystal. solvent |
|---|---|---|---|---|---|---|
| 66 | H | H | OH | ⟨phenyl⟩—CH$_3$ | S | 86 Hx |

TABLE 4-continued
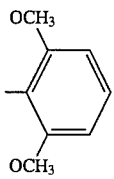
| Example No. | $R_a$ | $R'_a$ | Z | $R_V$ | M.p.; °C. crystal. C* solvent |
|---|---|---|---|---|---|
| 67 | H | H | OH | 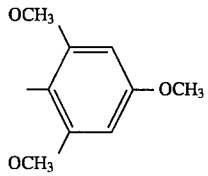 2,6-di-OCH$_3$ phenyl | S 107 Hx |
| 68 | H | H | OH | 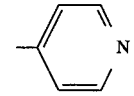 3,4,5-tri-OCH$_3$ phenyl | S 96 CH |
| 69 | H | H | OH | 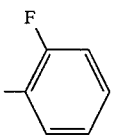 4-pyridyl | S 165 Hx (HCl) |
| 70 | 4-F | H | OH | 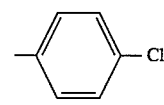 2-F phenyl | S 174 iPr$_2$O |
| 71 | 4-F | H | OH | 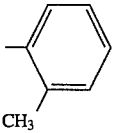 4-Cl phenyl | S 92 Hx |
| 72 | 4-F | H | OH | 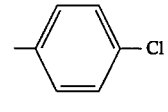 2-CH$_3$ phenyl | S 92 Hx |
| 73 | 4-Cl | H | OH | 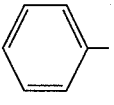 4-Cl phenyl | S 89 Hx |
| 74 | 4-t-Bu | H | OH | phenyl | S 88 CH |
| 75 | 2-Cl | 5-Cl | OH | 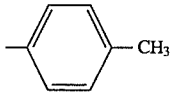 4-CH$_3$ phenyl | S 225 iPr$_2$O |

TABLE 4-continued
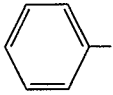
| Example No. | $R_a$ | $R'_a$ | Z | $R_V$ | C* | M.p.; °C. crystal. solvent |
|---|---|---|---|---|---|---|
| 76 | 3-Cl | 4-Cl | OH | 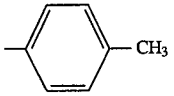 | S | 72 Hx |
| 77 | 3-Cl | 4-Cl | OH | 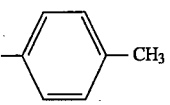 | R | 98 Hx |
| 78 | 3-Cl | 4-Cl | OH | 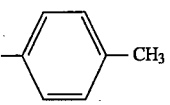 | S | 94 Pn |
| 79 | 3-Cl | 4-Cl | OH | 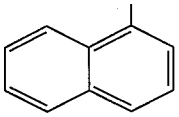 | S | 135 Hx |
| 80 | 2-Cl | 5-Cl | OH | 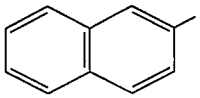 | S | 225 Hx |

TABLE 5

| Example n° | $R_a$ | $R'_a$ | $R_V$ | M.p.; °C. crystallisation solvent |
|---|---|---|---|---|
| 81 | H | H | 2,6-dimethoxyphenyl (OCH₃, OCH₃) | 161 iPr₂O |
| 82 | H | H | 3,4,5-trimethoxyphenyl | 201 AcOEt |
| 83 | H | H | 1-naphthyl | 190 iPr₂O |
| 84 | 4-F | H | 2-methylphenyl (CH₃) | 99 Hx |
| 85 | 4-Cl | H | 4-chlorophenyl (Cl) | 100 Hx |
| 86 | 4-t-Bu | H | phenyl | 88 Hx |
| 87 | 3-Cl | 4-Cl | phenyl | 83 Hx |
| 88 | 3-Cl | 4-Cl | 1-naphthyl | 90 Hx |

The compounds of Examples 81 to 88 are of S configuration.

TABLE 6

| No. | $R_3$ | $R_5$ | Naphthyl position | C* | M.p; °C. crystal. solvent |
|---|---|---|---|---|---|
| 89 | HO—CH₂—CH—CO₂H | H | 2 | S | 170 AcOEt |
| 90 | (CH₃)₂—CH—CH₂—CH—CO₂H | H | 1 | S | 88 Hx |

TABLE 6-continued

[Structure: Naphthyl (with R5) - pyrazole (with phenyl on N) - C(=O)-NH-R3]

| No. | R3 | R5 | Naphthyl position | C* | M.p; °C. crystal. solvent |
|---|---|---|---|---|---|
| 91 | CH₃—CH₂—CH(CH₃)—CH—CO₂H | H | 1 | S | 206 iPr₂O |
| 92 | CH₃—(CH₂)₂—CH—CO₂H | H | 1 | S | 198 iPr₂O |
| 93 | CH₃—(CH₂)₃—CH—CO₂H | H | 1 | R S | 92 CH |
| 94 | CH₃—(CH₂)₃—CH—CO₂H | H | 1 | R | 190 iPr₂O |
| 95 | cyclopentyl—CH—CO₂H | H | 1 | R S | 226 iPr₂O |
| 96 | (CH₃)₃—C—CH—CO₂H | H | 1 | S | 230 iPr₂O |
| 97 | CH₃—(CH₂)₂—CH—CO₂H | 6-OCH₃ | 2 | S | 92 Hx |
| 98 | CH₃—(CH₂)₃—CH—CO₂H | 6-OCH₃ | 2 | S | 98 CH |
| 99 | (CH₃)₂—CH—CH—CO₂H | 6-OCH₃ | 2 | S | 95 Hx |
| 100 | (CH₃)₂—CH—CH₂—CH—CO₂H | 6-OCH₃ | 2 | S | 95 Hx |
| 101 | (CH₃)₂—CH—CH₂—CH—CO₂H | H | 2 | S | 100 Hx |
| 102 | C₆H₅—(CH₂)₂—CH—CO₂H | H | 2 | S | 120 CH |
| 103 | C₆H₅—CH₂—CH—CO₂H | 6-OCH₃ | 2 | S | 95 Hx |
| 104 | HN=C(NH—NO₂)—NH—(CH₂)₃—CH—CO₂H | H | 2 | S | 175 AcOEt |

TABLE 6-continued

[Structure: naphthyl-substituted pyrazole with C(=O)-NH-R₃ group, N-phenyl, R₅ on naphthyl]

| No. | R₃ | R₅ | Naphthyl position | C* | M.p; °C. crystal. solvent |
|---|---|---|---|---|---|
| 105 | HN=C(NH-(CH₂)₃-CH(CO₂CH₃)-)-NH-NO₂ (nitroguanidino derivative) | H | 2 | S | 110 CH |
| 106 | indol-3-yl-CH₂-CH(CO₂H)- | H | 2 | S | 200 AcOEt |
| 107 | -CH(CO₂Na)-CH₂-S-CH₂-NH(COCH₃) | H | 2 | S | 217 EtOH |
| 108 | -CH(CO₂H)-CH₂-CH₂-C₆H₅ | H | 1 | S | 100 Hx |

TABLE 7

[Structure: pyrazole with R_IV at 4-position, R₅-phenyl at 5-position, R_a-phenyl at N1, C(=O)-NH-CH(COOH)-CH₂-C₆H₄-R₆ at 3-position]

| Example n° | R_a | R₆ | R_IV | R₅ | C* | M.p.; °C. crystallisation solvent |
|---|---|---|---|---|---|---|
| 109 | H | Cl | Cl | Cl | R S | 120 Hx |
| 110 | F | H | Cl | Cl | S | 110 Hx |
| 111 | F | Cl | Cl | Cl | R S | 100 Hx |

TABLE 8

Structures:
- Pyrazole with CO-N(R)(R₃OR) group, R_V at 5-position, R_I on N1
- Pyrazole with CO-N(R)(R₃) group, R_V at 5-position, R_Ia on N2

| Example No. | R_I | R_Ia | −N(R₃)(R) | R_V | C* | M.p.; °C. crystal solvent |
|---|---|---|---|---|---|---|
| 112 | CH₂–C₆H₅ (benzyl) | — | C₆H₅–CH(–NH–)–CO₂Na | 4-F-C₆H₄ | S | 158 iPr₂O |
| 113 | — | CH₂–C₆H₅ (benzyl) | C₆H₅–CH₂–CH(–NH–)–CO₂Na | 4-F-C₆H₄ | S | 130 iPr₂O |
| 114 | — | CH₂–C₆H₅ (benzyl) | (CH₃)₂–CH₂–CH(–NH–)–CO₂H | 6-methyl-naphth-2-yl | S | 80 Hx |
| 115 | — | CH₂–C₆H₅ (benzyl) | –N(H)–CH(cyclopentyl)–CO₂H | 6-methyl-naphth-2-yl | R S | 120 CH |
| 116 | — | CH₂–C₆H₅ (benzyl) | pyrrolidine-2-carboxylic acid (–N<CH₂CH₂CH₂CH(CO₂H)–) | 6-methyl-naphth-2-yl | S | 60 Hx |
| 117 | CH₂–C₆H₅ (benzyl) | — | –N(H)–CH(CO₂H)–(CH₂)₃–CH₃ | 2,6-(OCH₃)₂-3-methylphenyl | S | 69 Hx |
| 118 | — | CH₂–C₆H₅ (benzyl) | –N(H)–CH(CO₂H)–(CH₂)₃–CH₃ | 2,6-(OCH₃)₂-3-methylphenyl | S | 150 Hx |

TABLE 8-continued

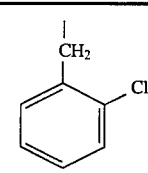

| Example No. | $R_I$ | $R_{Ia}$ | $-N\begin{smallmatrix}R_3\\R\end{smallmatrix}$ | $R_V$ | C* | M.p.; °C. crystal solvent |
|---|---|---|---|---|---|---|
| 119 | — | 2-Cl-benzyl (CH₂-C₆H₄-Cl) | -NH-CH(cyclohexyl)-CO₂H | 2,3-(OCH₃)₂-phenyl | S | 214 CH |
| 120 | 2-Cl-benzyl | — | -NH-CH(cyclohexyl)-CO₂H | 2,3-(OCH₃)₂-phenyl | S | 94 CH |
| 121 | benzyl | — | -NH-CH(cyclopentyl)-CO₂H | 2,3-(OCH₃)₂-phenyl | R S | 109 Hx |
| 122 | — | benzyl | -NH-CH(cyclopentyl)-CO₂H | 2,3-(OCH₃)₂-phenyl | R S | 173 Hx |

| TABLE 9 | | |
|---|---|---|

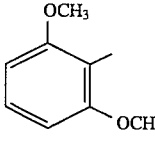

| Example n° | —R₃ | M.p.; °C. C* crystallisation solvent |
|---|---|---|
| 123 | (CH₃)₂—CH—CH—CO₂H | S 200 iPr₂O |
| 124 | C₆H₅—CH₂—CH—CO₂H | S 110 iPr₂O |

| TABLE 10 | | |
|---|---|---|

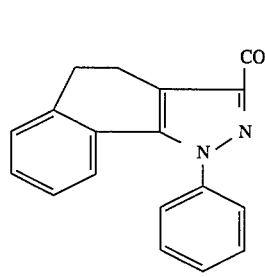

| Example n° | $-N\begin{smallmatrix}R\\R_3\end{smallmatrix}$ | M.p.; °C crystallisation solvent |
|---|---|---|
| 125 | C₆H₅—CH—CO₂H, NH— | 115 Pn |
| 126 | (CH₃)₂—CH—CH—CO₂H, NH— | 110 Hx |

TABLE 10-continued

Structure: 5-[(E)-2-(4-methylphenyl)ethenyl]-1-phenyl-1H-pyrazole-3-carboxamide with substituent —N(R)—R₃

| Example n° | —N(R)—R₃ | M.p.; °C crystallisation solvent |
|---|---|---|
| 127 | CH₃—(CH₂)₃—CH(NH—)—CO₂H | 90 Pn |
| 128 | (CH₃)₂—CH—CH₂—CH(NH—)—CO₂H | 100 Hx |
| 129 | CH₃—(CH₂)₃—CH(NH—)—CO₂H | 95 Pn |
| 130 | C₆H₅—CH₂—CH(NH—)—CO₂H | 100 Pn |

The compounds 125 to 130 are of S configuration.

TABLE 11

Structure: 5-aryl-1-naphthyl-1H-pyrazole-3-carboxamide with R₅, R'₅, R"₅ on phenyl; Rₐ on naphthyl; —N(R)—R₃ on carboxamide

| Ex n° | —N(R)—R₃ | Rₐ | R₅ | R'₅ | R"₅ | C* | M.p.; °C. crystal. solvent |
|---|---|---|---|---|---|---|---|
| 131 | (CH₃)₂—CH—CH(NH—)—CO₂H | H | H | H | H | S | 130 Hx |
| 132 | CH₃—(CH₂)₃—CH(NH—)—CO₂H | H | H | H | H | S | 100 Pn |
| 133 | (CH₃)₂—CH—CH₂—CH(NH—)—CO₂H | H | H | H | H | S | 220 Pn |
| 134 | C₆H₅—CH₂—CH(NH—)—CO₂H | H | H | H | H | S | 110 Pn |
| 135 | CH₃—(CH₂)₃—CH(NH—)—CO₂H | H | 2-OCH₃ | 6-OCH₃ | H | S | 113 |
| 136 | HN—CH(cyclopentyl)—CO₂H | H | 2-OCH₃ | 6-OCH₃ | H | S | 250 Pn |
| 137 | HN—CH(cyclopentyl)—CO₂H | H | 2-OCH₃ | 6-OCH₃ | H | R S | 136 Pn |

TABLE 11-continued

Structure:

$$\text{Pyrazole core with: 3-position } C(=O)-N(R)-R_3 \text{ amide; 5-position aryl with } R_5, R'_5, R''_5; \text{ N1-position naphthyl with } R_a$$

| Ex n° | −N(R)−R₃ | $R_a$ | $R_5$ | $R'_5$ | $R''_5$ | C* | M.p.; °C. crystal. solvent |
|---|---|---|---|---|---|---|---|
| 138 | −NH−CH(CO₂H)(phenyl) | H | 2-OCH₃ | 6-OCH₃ | H | S | 125 iPr₂O |
| 139 | −NH−C(CO₂H)(cyclopentyl ring) | H | 2-OCH₃ | 6-OCH₃ | H | — | 122 Hx |
| 140 | −NH−C(CO₂H)(cyclohexyl ring) | H | 2-OCH₃ | 6-OCH₃ | H | — | >260 Hx |
| 141 | −NH−CH(CO₂H)−CH₂−phenyl | H | 2-OCH₃ | 6-OCH₃ | H | S | 112 iPr₂O |
| 142 | −NH−CH(CO₂H)−(CH₂)₃−CO₂H | H | 2-OCH₃ | 6-OCH₃ | H | S | 110 iPr₂O |
| 143 | −NH−C(CH₃)(CO₂H)(cyclopropyl) | H | 2-OCH₃ | 6-OCH₃ | H | R S | 116 iPr₂O |
| 144 | −NH−C(CO₂H)(cycloheptyl ring) | H | 2-OCH₃ | 6-OCH₃ | H | — | >260 Hx |
| 145 | −NH−C(CO₂H)(4-methylcyclohexyl ring) | H | 2-OCH₃ | 6-OCH₃ | H | — | >260 Hx |
| 146 | −NH−CH(CO₂H)(cycloheptyl) | H | 2-OCH₃ | 6-OCH₃ | H | R S | >260 Hx |
| 147 | −NH−CH(CO₂H)(cyclohexyl) | H | 2-OCH₃ | 6-OCH₃ | H | S | >260 Hx |

TABLE 11-continued

[Structure: pyrazole with C(=O)-N(R)-R3 group, R5/R'5/R"5-substituted phenyl, and naphthyl-Ra substituent]

| Ex n° | —N(R)—R3 | Ra | R5 | R'5 | R"5 | C* | M.p.; °C. crystal. solvent |
|---|---|---|---|---|---|---|---|
| 148 | —NH—CH(cyclopentyl)—CO2H | H | 2-OCH3 | 5-OCH3 | H | R S | 99 iPr2O |
| 149 | —NH—CH(cyclopentyl)—CO2H | H | 2-OCH3 | 4-OCH3 | H | R S | 110 iPr2O |
| 150 | —NH—CH(cyclohexyl)—CO2H | H | 2-OCH3 | 5-OCH3 | H | S | 223 iPr2O |
| 151 | —NH—CH(cyclohexyl)—CO2H | H | 2-OCH3 | 4-OCH3 | H | S | 109 iPr2O |
| 152 | —NH—CH(cyclopentyl)—CO2H | H | 2-OCH3 | 6-OCH3 | H | R | 247 iPr2O |
| 153 | —NH—C(cyclopropyl)(CO2H) | H | 2-OCH3 | 6-OCH3 | H | — | 128 Hx |
| 154 | —NH—C(CH3)(cyclohexyl)—CO2H | H | 2-OCH3 | 6-OCH3 | H | R S | 132 iPr2O |
| 155 | —NH—C(cyclobutyl)(CO2H) | H | 2-OCH3 | 6-OCH3 | H | — | 114 Hx |
| 156 | —NH—CH(C(CH3)3)—CO2H | H | 2-OCH3 | 6-OCH3 | H | S | 149 iPr2O |

TABLE 11-continued

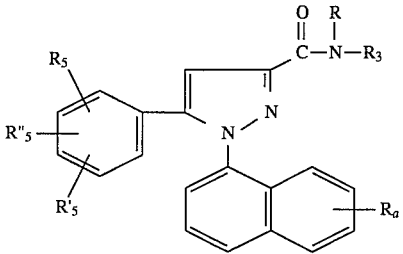

| Ex n° | −N(R)−R3 | Ra | R5 | R'5 | R"5 | C* | M.p.; °C. crystal. solvent |
|---|---|---|---|---|---|---|---|
| 157 | −NH−C(CH3)2−CO2H | H | 2-OCH3 | 6-OCH3 | H | — | 244 iPr2O |
| 158 | −NH−CH(CO2H)−(CH2)5−CH3 | H | 2-OCH3 | 6-OCH3 | H | R S | 106 Hx |
| 159 | −NH−CH(CO2H)−cycloheptyl | H | 2-OCH3 | 6-OCH3 | H | S | >260 Hx |
| 160 | −NH−CH(CO2H)−cycloheptyl | H | 2-OCH3 | 6-OCH3 | H | R | >260 Hx |
| 161 | −NH−C(CO2H)−(CH2)11− (cyclic) | H | 2-OCH3 | 6-OCH3 | H | — | 174 Hx |
| 162 | −NH−(norbornyl)−CO2H | H | 2-OCH3 | 6-OCH3 | H | R S | >260 EtOH |
| 163 | −NH−C(Ph)2−CO2H | H | 2-OCH3 | 6-OCH3 | H | — | 244 iPr2O |
| 164 | −NH−CH(CO2H)−cyclohexyl | H | 2-OC2H5 | 6-OC2H5 | H | S | 222 Hx |
| 165 | −NH−C(CO2H)(piperidinyl-N−CH2−Ph) | H | 2-OCH3 | 6-OCH3 | H | — | 190 Et2O |

TABLE 11-continued

| Ex n° | R<br>|<br>—N—R₃ | Rₐ | R₅ | R'₅ | R"₅ | C* | M.p.; °C.<br>crystal.<br>solvent |
|---|---|---|---|---|---|---|---|
| 166 | 2-amino-1,2,3,4-tetrahydronaphthalene-2-CO₂H | H | 2-OCH₃ | 6-OCH₃ | H | R S | 170<br>CH₂Cl₂ |
| 167 | 4-amino-4-CO₂H-piperidine, HCl | H | 2-OCH₃ | 6-OCH₃ | H | — | 280<br>Et₂O |
| 168 | 2-amino-2-CO₂H-adamantane | H | 2-OC₂H₅ | 6-OC₂H₅ | H | — | >260<br>iPr₂O |
| 169 | β,β,β',β'-tetramethyl amino-CO₂H-N—H | H | 2-OCH₃ | 6-OCH₃ | H | — | >260<br>H₂O |
| 170 | quinuclidine-amino-CO₂H | H | 2-OCH₃ | 6-OCH₃ | H | R S | >260<br>CH₂Cl₂<br>—Et₂O |
| 171 | bicyclic amino-CO₂H | H | 2-OCH₃ | 6-OCH₃ | H | — | >260<br>iPr₂O |
| 172 | proline (—N pyrrolidine-CO₂H) | H | 2-OCH₃ | 6-OCH₃ | H | S | 120<br>Pn |
| 173 | —NH—CH(cyclopentyl)—CO₂CH₃ | H | 2-OCH₃ | 6-OCH₃ | H | R S | 81<br>Pn |
| 174 | —NH—CH(cyclopentyl)—CONH₂ | H | 2-OCH₃ | 6-OCH₃ | H | R S | >260<br>iPr₂O |

TABLE 11-continued

| Ex n° | R<br>\|<br>—N—R$_3$ | R$_a$ | R$_5$ | R'$_5$ | R"$_5$ | C* | M.p.; °C.<br>crystal.<br>solvent |
|---|---|---|---|---|---|---|---|
| 175 | CH$_3$, -N-CH(cyclopentyl)-CO$_2$H | H | 2-OCH$_3$ | 6-OCH$_3$ | H | R S | 217<br>Hx |
| 176 | indoline-2-carboxylic acid (HO$_2$C) | H | 2-OCH$_3$ | 6-OCH$_3$ | H | R S | >260<br>iPr$_2$O |
| 177 | tetrahydrothienopyridine-CO$_2$H | H | 2-OCH$_3$ | 6-OCH$_3$ | H | R S | 130<br>iPr$_2$O |
| 178 | H, -N-CH-CO$_2$H (cyclopentyl) | H | 2-OCH$_3$ | 4-OCH$_3$ | 6-OCH$_3$ | R S | 229<br>iPr$_2$O |
| 179 | H, -N-CH-CO$_2$H (cyclohexyl) | H | 2-OCH$_3$ | 4-OCH$_3$ | 6-OCH$_3$ | S | >260<br>iPr$_2$O |
| 180 | H, -N-CH-CO$_2$H (cyclopentyl) | 4-Cl | 2-OCH$_3$ | 6-OCH$_3$ | H | R S | 125<br>Hx |
| 181 | H, -N-CH-(CH$_2$)$_3$-CH$_3$, CO$_2$H | 4-Cl | 2-OCH$_3$ | 6-OCH$_3$ | H | S | 120<br>Hx |
| 182 | prolyl -N(CO$_2$H) | 4-Cl | 2-OCH$_3$ | 6-OCH$_3$ | H | S | 140<br>CH |
| 183 | H, -N-adamantyl-CO$_2$H | H | 2-CH$_3$ | 6-CH$_3$ | H | — | 280<br>Et$_2$O |

TABLE 11-continued

| Ex n° | R / -N-R3 (substituent) | Ra | R5 | R'5 | R"5 | C* | M.p.; °C. crystal. solvent |
|---|---|---|---|---|---|---|---|
| 184 | -NH-C(cyclopropyl)(cyclopropyl)-CO2H | H | 2-OCH3 | 6-OCH3 | H | — | 225 Hx |
| 185 | -NH-CH2-CO2H | H | 2-OCH3 | 6-OCH3 | H | — | 206 iPr2O |
| 186 | -NH-adamantyl-CO2H | 4-Cl | 2-OCH3 | 6-OCH3 | H | — | >260 iPr2O |
| 187 | -NH-(4-tetrahydropyranyl)-CO2H | H | 2-OCH3 | 6-OCH3 | H | — | 180 MeOH —H2O |
| 188 | HN-(thiochroman-3-yl)-COO⊖K⊕ | H | 2-OCH3 | 6-OCH3 | H | R S | >260 Et2O |
| 189 | -NH-CH(CO2H)-CH2-cyclohexyl | H | 2-OCH3 | 6-OCH3 | H | S | 109 CH |
| 190 | bicyclic-NH-, CO2H | H | 2-OCH3 | 6-OCH3 | H | R S | 130 CH |

TABLE 12

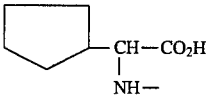

| Ex. n° | $R_a$ | $R'_a$ | $R''_a$ | $-\underset{R_3}{\underset{|}{N}}-\overset{R}{\underset{}{}}$ | $R_5$ | $R'_5$ | $R''_5$ | C* | M.p; °C. crystal. solvent |
|---|---|---|---|---|---|---|---|---|---|
| 191 | H | H | H | $CH_3-(CH_2)_3-\underset{NH-}{\underset{|}{\overset{CO_2H}{\overset{|}{CH}}}}$ | 3-OCH$_3$ | 4-OCH$_3$ | H | S | 79 Hx |
| 192 | H | H | H | $CH_3-(CH_2)_3-\underset{NH-}{\underset{|}{\overset{CO_2H}{\overset{|}{CH}}}}$ | 3-OCH$_3$ | 4-OCH$_3$ | 5-OCH$_3$ | S | 69 Hx |
| 193 | H | H | H | $CH_3-(CH_2)_3-\underset{NH-}{\underset{|}{\overset{CO_2H}{\overset{|}{CH}}}}$ | 2-OCH$_3$ | 4-OCH$_3$ | 6-OCH$_3$ | S | 90 Hx |
| 194 | H | H | H | $C_6H_5-\underset{CH_2-NH-}{\underset{|}{CH-CO_2H}}$ | 2-OCH$_3$ | 6-OCH$_3$ | H | R S | 94 Hx |
| 195 | 3-Cl | 4-Cl | H | $CH_3-(CH_2)_3-\underset{NH-}{\underset{|}{\overset{CO_2H}{\overset{|}{CH}}}}$ | 2-OCH$_3$ | 6-OCH$_3$ | H | S | 94 Hx |
| 196 | 3-Cl | 4-Cl | H | 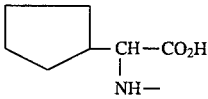 | 2-OCH$_3$ | 6-OCH$_3$ | H | R S | 100 CH |
| 197 | 2-Cl | 6-Cl | H | $CH_3-(CH_2)_3-\underset{NH-}{\underset{|}{\overset{CO_2H}{\overset{|}{CH}}}}$ | 2-OCH$_3$ | 6-OCH$_3$ | H | S | 223 Pn |
| 198 | 2-Cl | 5-Cl | H | $CH_3-(CH_2)_3-\underset{NH-}{\underset{|}{\overset{CO_2H}{\overset{|}{CH}}}}$ | 2-OCH$_3$ | 6-OCH$_3$ | H | S | 90 Pn |
| 199 | 3-Cl | 4-Cl | H | $C_6H_5-(CH_2)_2-\underset{|}{\overset{CO_2H}{\overset{|}{CH}}}-NH-$ | H | H | H | S | 85 CH |
| 200 | 3-Cl | 4-Cl | H | $CH_3-(CH_2)_3-\underset{NH-}{\underset{|}{\overset{CO_2H}{\overset{|}{CH}}}}$ | H | H | H | S | 78 Hx |
| 201 | 3-Cl | 4-Cl | H | cyclopentyl-CH(NH-)-CO$_2$H | H | H | H | R S | 84 Hx |

TABLE 12-continued

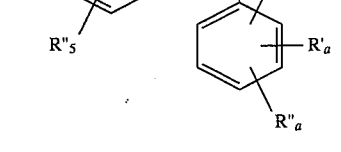

| Ex. n° | $R_a$ | $R'_a$ | $R"_a$ | $\underset{R}{\overset{\|}{-N-R_3}}$ | $R_5$ | $R'_5$ | $R"_5$ | C* | M.p; °C. crystal. solvent |
|---|---|---|---|---|---|---|---|---|---|
| 202 | 4-t-Bu | H | H | $CH_3-(CH_2)_3-\underset{NH-}{\overset{CO_2H}{\overset{\|}{CH}}}$ | H | H | H | S | 85 Hx |
| 203 | H | H | H | $(CH_3)_2-CH-CH_2$ $H_2N-\underset{O}{\overset{\|}{C}}-\underset{NH-}{\overset{\|}{CH}}$ | H | H | H | S | 66 Hx |
| 204 | 3-Cl | 4-Cl | H | $CH_3-(CH_2)_3-\underset{NaOOC}{\overset{NH-}{\overset{\|}{CH}}}$ | 2-$OCH_3$ | 6-$OCH_3$ | H | S | 146 $H_2O$ |
| 205 | 3-Cl | 4-Cl | H | $CH_3-(CH_2)_3-\underset{NH-}{\overset{CO_2H}{\overset{\|}{CH}}}$ | 2-$OCH_3$ | 4-OCH3 | 6-$OCH_3$ | S | 98 CH |
| 206 | 2-Cl | 5-Cl | H | $-\underset{}{\overset{H}{\overset{\|}{N}}}-\underset{CO_2CH_3}{\overset{\|}{CH}}-(CH_2)_3-CH_3$ | 2-$OCH_3$ | 6-$OCH_3$ | H | S | 64 Pn |
| 207 | 2-Cl | 3-Cl | 4-Cl | $-\overset{H}{\overset{\|}{N}}-\underset{\text{cyclopentyl}}{\overset{\|}{CH}}-CO_2H$ | 2-$OCH_3$ | 6-$OCH_3$ | H | R,S | 120 CH |
| 208 | 2-Cl | 3-Cl | 4-Cl | $-\overset{H}{\overset{\|}{N}}-\underset{CO_2H}{\overset{\|}{CH}}-(CH_2)_3-CH_3$ | 2-$OCH_3$ | 6-$OCH_3$ | H | S | 219 Pn |
| 209 | 2-Cl | 4-Cl | 6-Cl | $-\overset{H}{\overset{\|}{N}}-\underset{CO_2H}{\overset{\|}{CH}}-(CH_2)_3-CH_3$ | 2-$OCH_3$ | 6-$OCH_3$ | H | S | 220 Pn |
| 210 | 2-Cl | 4-Cl | 6-Cl | $-\overset{H}{\overset{\|}{N}}-\underset{\text{cyclopentyl}}{\overset{\|}{CH}}-CO_2H$ | 2-$OCH_3$ | 6-$OCH_3$ | H | R S | 210 CH |
| 211 | 3-$CF_3$ | 5-$CF_3$ | H | $-\overset{H}{\overset{\|}{N}}-\underset{CO_2H}{\overset{\|}{CH}}-(CH_2)_3-CH_3$ | 2-$OCH_3$ | 6-$OCH_3$ | H | S | 79 Pn |

TABLE 12-continued
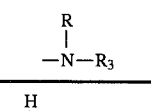
| Ex. n° | $R_a$ | $R'_a$ | $R''_a$ | $-\underset{R_3}{\overset{R}{N}}-$ | $R_5$ | $R'_5$ | $R''_5$ | C* | M.p; °C. crystal. solvent |
|---|---|---|---|---|---|---|---|---|---|
| 212 | 3-CF$_3$ | 5-CF$_3$ | H | 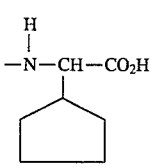 | 2-OCH$_3$ | 6-OCH$_3$ | H | R S | 181 Hx |
| 213 | 2-Cl | 3-Cl | H | 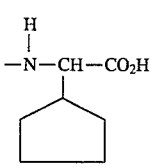 | 2-OCH$_3$ | 6-OCH$_3$ | H | R,S | 112 Hx |
| 214 | 2-Cl | 3-Cl | H | 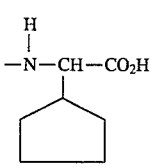 | 2-OCH$_3$ | 6-OCH$_3$ | H | S | 108 Pn |
| 215 | 2-Cl | 5-Cl | H | 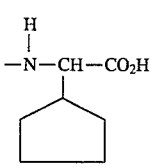 | 4-NO$_2$ | H | H | R S | 115 Hx |
| 216 | 2-Cl | 3-Cl | H | 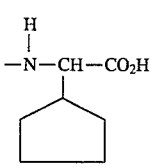 | 2-OCH$_3$ | 6-OCH$_3$ | H | S | 114 Hx |
| 217 | 3-CF$_3$ | 5-CF$_3$ | H | 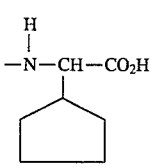 | 2-OCH$_3$ | 6-OCH$_3$ | H | S | 94 Hx |
| 218 | 3-CF$_3$ | 5-CF$_3$ | H | 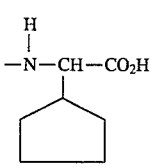 | 2-OCH$_3$ | 6-OCH$_3$ | H | S | 70 CH |
| 219 | 2-Cl | 4-Cl | 6-Cl | 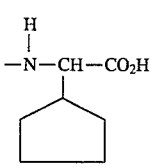 | 2-OCH$_3$ | 6-OCH$_3$ | H | S | 110 Hx |
| 220 | 3-Cl | 4-Cl | H | 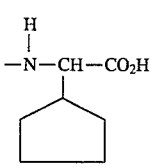 | 2-Cl | 6-Cl | H | — | 240 iPr$_2$O |

TABLE 12-continued

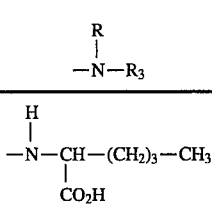

| Ex. n° | $R_a$ | $R'_a$ | $R''_a$ | $-\overset{R}{\underset{\|}{N}}-R_3$ | $R_5$ | $R'_5$ | $R''_5$ | C* | M.p; °C. crystal. solvent |
|---|---|---|---|---|---|---|---|---|---|
| 221 | 3-Cl | 4-Cl | H | $-\underset{}{\overset{H}{N}}-\underset{CO_2H}{\overset{\|}{CH}}-(CH_2)_3-CH_3$ | 2-Cl | 6-Cl | H | S | 98 Pn |
| 222 | 3-Cl | 4-Cl | H | $-\underset{}{\overset{H}{N}}-\underset{CO_2H}{\overset{\|}{CH}}-C_6H_5$ | 2-Cl | 6-Cl | H | S | 120 CH |
| 223 | 3-Cl | 4-Cl | H | $-\underset{}{\overset{H}{N}}-CH-CO_2H$ (cyclopentyl) | 2-Cl | 6-Cl | H | R S | 212 Pn |
| 224 | 2-Cl | 4-Cl | H | $-\underset{}{\overset{H}{N}}-CH-CO_2H$ (cyclopentyl) | 2-OCH$_3$ | 6-OCH$_3$ | H | R S | 124 Hx |
| 225 | 2-Cl | 4-Cl | H | $-\underset{}{\overset{H}{N}}-\underset{CO_2H}{\overset{\|}{CH}}-(CH_2)_3-CH_3$ | 2-OCH$_3$ | 6-OCH$_3$ | H | S | 196 Hx |
| 226 | 3-Cl | 4-F | H | $-\underset{}{\overset{H}{N}}-CH-CO_2H$ (cyclopentyl) | 2-OCH$_3$ | 6-OCH$_3$ | H | R S | 110 CH |
| 227 | 3-Cl | 4-Cl | H | $-\underset{}{\overset{H}{N}}-CH-CO_2H$ (cyclopentyl) | 2-F | 6-F | H | R S | 86 iPr$_2$O |
| 228 | 3-Cl | 4-Cl | H | $-\underset{}{\overset{H}{N}}-\underset{CO_2H}{\overset{\|}{CH}}-(CH_2)_3-CH_3$ | 2-F | 6-F | H | S | 76 Hx |
| 229 | 2-Cl | 5-Cl | H | $-\underset{}{\overset{H}{N}}-\underset{CO_2H}{\overset{\|}{CH}}-CH_2-C_6H_{11}$ | 2-OCH$_3$ | 6-OCH$_3$ | H | S | 86 iPr$_2$O |

TABLE 12-continued

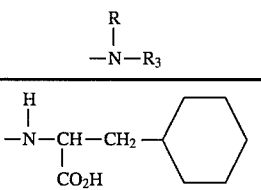

| Ex. n° | $R_a$ | $R'_a$ | $R''_a$ | $-\underset{R_3}{\overset{R}{N}}-$ | $R_5$ | $R'_5$ | $R''_5$ | C* | M.p; °C. crystal. solvent |
|---|---|---|---|---|---|---|---|---|---|
| 230 | 2-Cl | 6-Cl | H | −NH−CH(CO₂H)−CH₂−cyclohexyl | 2-OCH₃ | 6-OCH₃ | H | S | 268 iPr₂O |
| 231 | H | H | H | −NH−CH(CO₂H)−(CH₂)₃−CH₃ | 2-OCH₃ | 4-OCH₃ | H | S | 76 Hx |
| 232 | H | H | H | −NH−CH(CO₂H)−CH₂−phenyl | 4-NO₂ | H | H | S | 100 Hx |
| 233 | 4-Cl | H | H | −NH−CH(cyclopentyl)−CO₂H | 2-OCH₃ | 6-OCH₃ | H | R S | 116 CH |
| 234 | 4-Cl | H | H | −NH−CH(CO₂H)−(CH₂)₃−CH₃ | 2-OCH₃ | 6-OCH₃ | H | S | 169 Hx |
| 235 | 2-Cl | H | H | −NH−CH(cyclopentyl)−CO₂H | 2-OCH₃ | H | H | R S | 90 CH |
| 236 | 2-Cl | H | H | −NH−CH(CO₂H)−(CH₂)₃−CH₃ | 2-OCH₃ | H | H | S | 87 Hx |
| 237 | 3-Cl | 4-Cl | H | −NH−CH(cyclopentyl)−CO₂H | 2-OCH₃ | H | H | R S | 100 Hx |
| 238 | 3-Cl | 4-Cl | H | −NH−CH(CO₂H)−(CH₂)₃−CH₃ | 2-OCH₃ | H | H | S | 85 Pn |

TABLE 12-continued

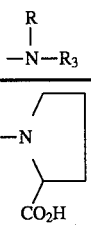

| Ex. n° | $R_a$ | $R'_a$ | $R''_a$ | $-\underset{R}{N}-R_3$ | $R_5$ | $R'_5$ | $R''_5$ | C* | M.p; °C. crystal. solvent |
|---|---|---|---|---|---|---|---|---|---|
| 239 | 2-Cl | 5-Cl | H | -N⟨pyrrolidine-CO₂H⟩ | 2-OCH₃ | 6-OCH₃ | H | S | 107 Hx |
| 240 | 3-Cl | 4-F | H | -NH-CH(CO₂H)-(CH₂)₃-CH₃ | 2-OCH₃ | 6-OCH₃ | H | S | 96 iPr₂O |
| 241 | 3-Cl | H | H | -NH-CH(cyclopentyl)-CO₂H | 2-OCH₃ | 6-OCH₃ | H | R S | 103 CH |
| 242 | 3-Cl | H | H | -NH-CH(cyclopentyl)-(CH₂)₃-CH₃ with CO₂H | 2-OCH₃ | 6-OCH₃ | H | S | 83 CH |
| 243 | 3-Cl | 4-Cl | H | -NH-CH(cyclopentyl)-CO₂H | 2-CH₃ | H | H | R,S | 86 Hx |
| 244 | 3-Cl | 4-Cl | H | -NH-CH(CO₂H)-(CH₂)₃-CH₃ | 2-CH₃ | H | H | S | 85 Pn |
| 245 | 3-Cl | 5-Cl | H | -NH-CH(cyclopentyl)-CO₂H | 2-OCH₃ | 6-OCH₃ | H | R S | 109 Hx |
| 246 | 3-Cl | 5-Cl | H | -NH-CH(CO₂H)-(CH₂)₃-CH₃ | 2-OCH₃ | 6-OCH₃ | H | S | 97 Pn |
| 247 | H | H | H | -NH-CH(CO₂H)-(CH₂)₃-CH₃ | 2-OCH₃ | 6-OCH₃ | H | S | 92 Pn |

TABLE 13

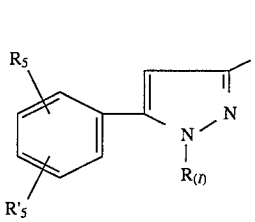

| Ex. n° | R₅ | R'₅ | R_(I) | —N(R)—R₃ | C* | M.p.; °C. crystallisation solvent |
|---|---|---|---|---|---|---|
| 248 | 2-OCH₃ | 6-OCH₃ | 4-methyl-7-chloroquinolin-2-yl | —NH—CH(cyclopentyl)—CO₂CH₃ | R S | 107 Pn |
| 249 | 2-OCH₃ | 6-OCH₃ | 4-methyl-7-chloroquinolin-2-yl | —NH—CH(cyclopentyl)—CO₂H | R S | 131 iPr₂O |
| 250 | 2-OCH₃ | 6-OCH₃ | 2-methylquinolin-3-yl | —NH—CH(cyclopentyl)—CO₂CH₃ | R S | 111 Pn |
| 251 | 2-OCH₃ | 6-OCH₃ | 2-methylbenzothiazol-3-yl | —NH—CH(cyclopentyl)—CO₂H | R S | 112 iPr₂O |
| 252 | 2-OCH₃ | 6-OCH₃ | 2-methylquinolin-3-yl | —NH—CH(cyclohexyl)—CO₂H | S | 117 iPr₂O |
| 253 | 2-OCH₃ | 6-OCH₃ | 4-methyl-7-chloroquinolin-2-yl | —NH—CH(cyclohexyl)—CO₂H | S | 142 iPr₂O |
| 254 | 2-OCH₃ | 6-OCH₃ | 8-methylquinolin-2-yl | —NH—C(adamantyl)—CO₂H | — | 200 iPr₂O |
| 255 | 2-OCH₃ | 6-OCH₃ | 8-methylquinolin-2-yl | —NH—CH(cyclohexyl)—CO₂H | S | 260 iPr₂O |
| 256 | 2-OCH₃ | 6-OCH₃ | methylcyclohexyl | —NH—CH(cyclopentyl)—CO₂H | R S | 118 Pn |

TABLE 13-continued

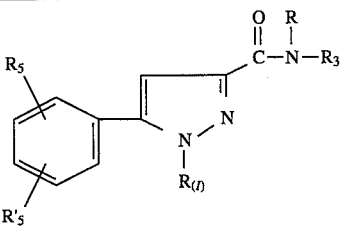

| Ex. n° | R$_5$ | R'$_5$ | R$_{(I)}$ | $-\underset{R_3}{\overset{R}{N}}-$ | C* | M.p.; °C. crystallisation solvent |
|---|---|---|---|---|---|---|
| 257 | 2-OCH$_3$ | 6-OCH$_3$ | cyclohexyl | pyrrolidine-CO$_2$H | S | 128 Pn |
| 258 | 2-OCH$_3$ | 6-OCH$_3$ | cyclohexyl | $-\text{N}H-\text{CH}(\text{CO}_2\text{H})-(\text{CH}_2)_3-\text{CH}_3$ | S | 110 Pn |
| 259 | 2-OCH$_3$ | 6-OCH$_3$ | tetrahydronaphthyl | $-\text{N}H-\text{CH}(\text{CO}_2\text{H})-$cyclohexyl | S | >260 iPr$_2$O |
| 260 | 2-OCH$_3$ | 6-OCH$_3$ | tetrahydronaphthyl | adamantyl-NH-, CO$_2$H | — | >260 iPr$_2$O |
| 261 | 2-OCH$_3$ | 6-OCH$_3$ | phthalhydrazide | adamantyl-NH-, CO$_2$H | — | >260 iPr$_2$O |
| 262 | 2-OCH$_3$ | 6-OCH$_3$ | benzothiadiazole | adamantyl-NH-, CO$_2$H | — | >260 iPr$_2$O |

TABLE 14

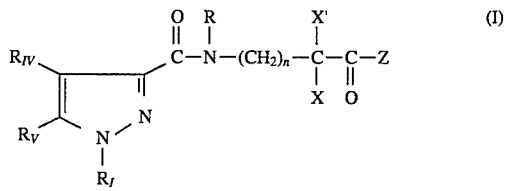

| Example nº | R₃ | C* | M.p.; °C. crystallisation solvent |
|---|---|---|---|
| 263 | C₆H₅—CH₂—CH(—)—CO₂H | S | 105 Pn |
| 264 | C₆H₅—CH₂—CH(—)—CO₂CH₃ | S | 80 Pn |

TABLE 15

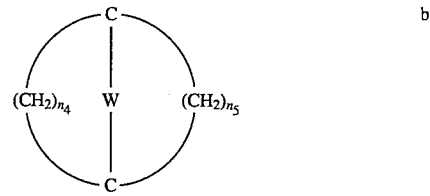

| Example nº | —N(R)(R₃) | C* | M.p.; °C. crystallisation solvent |
|---|---|---|---|
| 265 | —NH—CH(CO₂H)—(CH₂)₃—CH₃ | S | 110 iPr₂O |
| 266 | —NH—CH(cyclopentyl)—CO₂H | R S | 120 iPr₂O |
| 267 | —N(pyrrolidine-2-CO₂H) | S | 125 CH |

We claim:
1. A 3-amidopyrazole of formula (I):

$$R_{IV}-\underset{R_V}{\underset{|}{C}}=\underset{\underset{R_I}{|}}{\underset{N}{N}}-\overset{O}{\overset{\|}{C}}-\underset{\underset{R}{|}}{N}-(CH_2)_n-\overset{X'}{\underset{\underset{X}{|}}{C}}-\overset{}{\underset{\underset{O}{\|}}{C}}-Z \quad (I)$$

in which:

X and X', together with the carbon atom to which they are linked, form a cycle of formula b:

$$\text{(cycle b with W, } (CH_2)_{n_4}, (CH_2)_{n_5}\text{)}$$

in which W is a carbon atom, $n_4$ is 3, and $n_5$ is 3; the cycle of formula b is attached to >N—R and to C(C))—Z through one carbon atom of one or other of the two rings; and the cycle b is optionally substituted on one and/or the other of the rings with one or two $C_1$–$C_4$ alkyl groups;

$R_1$ represents:
 a phenyl group substituted by $R_a$, $R'_a$ and $R''_a$, wherein $R_a$, $R'_a$ and $R''_a$ each independently represent a hydrogen atom, a halogen atom, a hydroxyl group, a linear or branched $C_1$–$C_4$ alkyl group, a $C_1$–$C_4$ alkoxy group, a trifluoromethyl group, a trifluoromethoxy group, a nitro group, a carboxyl group or an amino group;
 a tetrahydronaphthyl group; or
 a naphthyl group substituted with $R_a$, $R'_a$ and $R''_a$ as defined above;

R represents hydrogen or linear or branched $C_1$–$C_4$ alkyl group;

n represents 0, 1, 2 or 3;

Z represents
 a hydroxyl group;
 a $C_1$–$C_6$ alkoxy group;
 an oxygen atom substituted with a carboxylic acid-protecting group, wherein the carboxylic acid-protecting group is selected from the group consisting of tert-butyl, benzyl, benzyl substituted with a halogen atom, $C_1$–$C_6$ alkyl, trifluoromethyl, trifluoromethoxy or carboxyl group;
 an amino group; or
 a nitrogen atom substituted with a carboxyalkyl group in which the alkyl group is a linear or branched $C_1$–$C_6$ group;

$R_{IV}$ represents a hydrogen atom, a halogen atom or a $C_1$–$C_6$ alkyl group;

$R_V$ represents:
 a phenyl group substituted by $R_5$, $R'_5$ and $R''_5$, where $R_5$, $R'_5$ and $R''_5$ each independently represent a hydrogen atom, a halogen atom, a linear or branched $C_1-C_4$ alkyl group, a hydroxyl group, a $C_1-C_4$ alkoxy group, a nitro group, a trifluoromethyl group, a trifluoromethoxy group, a cyano group, an amino group, a carboxyl group, a $C_1-C_4$ carboxyalkyl group or a phenyl group;

a naphthyl group unsubstituted or substituted with a $C_1-C_4$ alkyl;

a styryl group unsubstituted or substituted with a $C_1-C_4$ alkyl group;

or alternatively $R_{IV}$ and $R_V$ considered together represent:

a group

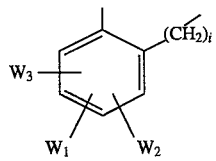

in which the phenyl group substitutes the pyrazole at position 5 and the group —$(CH_2)_i$— in which i=1 to 3 substitutes the pyrazole at position 4; $W_1$, $W_2$ and $W_3$ substitute the benzene ring and independently represent hydrogen, a halogen atom or a hydroxyl group;

or one of its pharmaceutically acceptable, crystallization or separation salts with organic or inorganic acids or with inorganic or organic bases.

2. A pharmaceutical composition comprising an effective amount of a compound according to claim 1 or a pharmaceutically acceptable salt thereof and at least one pharmaceutically acceptable excipient.

3. A pharmaceutical composition according to claim 2 in the form of a dosage unit.

4. A pharmaceutical composition according to claim 3 wherein the effective amount is from 1 to 250 mg the compound or a pharmaceutically acceptable salt thereof.

5. A compound according to claim 1, wherein $R_I$ represents a naphthyl group substituted by $R_a$, $R'_a$ and $R''_a$ wherein $R_a$ $R'_a$ and $R''_a$ each independently represent a hydrogen atom, a halogen atom, a hydroxyl group, a linear or branched $C_1-C_4$ alkyl group, a $C_1-C_4$ alkoxy group, a trifluoromethyl group, a trifluoromethoxy group, a nitro group, a carboxyl group or an amino group; or $R_I$ represents a phenyl group substituted with $R_a$, $R'_a$, and $R''_a$ as defined above.

6. A compound according to claim 1, wherein $R_V$ represents a phenyl group substituted by $R_5$, $R'_5$ and $R''_5$, where $R_5$, $R'_5$ and $R''_5$ each independently represent a hydrogen atom, a halogen atom, a linear or branched $C_1-C_4$ alkyl group, a hydroxyl group, a $C_1-C_4$ alkoxy group, a nitro group, a trifluoromethyl group, a trifluoromethoxy group, a cyano group, an amino group, a carboxyl group, a $C_1-C_4$ carboxyalkyl group or a phenyl group.

7. A compound according to claim 6, wherein $R_5$, $R'_5$ or $R''_5$ is hydrogen or a $C_1-C_4$ alkoxy group.

8. A compound according to claim 5, wherein $R_I$ represents a napthyl group substituted by $R_a$, $R'_a$ and $R''_a$, wherein $R_a$, $R'_a$ and $R''_a$ each independently represent a hydrogen atom, a halogen atom, a hydroxyl group, a linear or branched $C_1-C_4$ alkyl group, a $C_1-C_4$ alkoxy group, a trifluoromethyl group, a trifluoromethoxy group, a nitro group, a carboxyl group or an amino group; or a naphthyl group substituted with $R_a$, $R'_a$, and $R''_a$ as defined above; and $R_V$ represents a phenyl group substituted by $R_5$, $R'_5$ and $R''_5$, where $R_5$, $R'_5$ and $R''_5$ each independently represent a hydrogen atom, a halogen atom, a linear or branched $C_1-C_4$ alkyl group, a hydroxyl group, a $C_1-C_4$ alkoxy group, a nitro group, a trifluoromethyl group, a trifluoromethoxy group, a cyano group, an amino group, a carboxyl group, a $C_1-C_4$ carboxyalkyl group or a phenyl group.

9. A compound according to claim 8, wherein R represents a hydrogen atom, n represents 0, Z represents a hydroxyl group, $R_{IV}$ represents a hydrogen atom, $R_V$ represents a phenyl group substituted by $R_5$, $R'_5$ and $R''_5$ wherein $R_5$ is hydrogen, and $R'_5$ and $R''_5$ are each $C_{1-4}$ alkoxy.

10. A compound according to claim 9, wherein $R'_5$ and $R''_5$ are each methoxy and wherein $R_I$ represents an unsubstituted naphthyl group.

11. A pharmaceutical composition comprising an effective amount of a compound according to claim 5 or a pharmaceutically acceptable salt thereof and at least one pharmaceutically acceptable excipient.

12. A pharmaceutical composition comprising an effective amount of a compound according to claim 6 or a pharmaceutically acceptable salt thereof and at least one pharmaceutically acceptable excipient.

13. A pharmaceutical composition comprising an effective amount of a compound according to claim 7 or a pharmaceutically acceptable salt thereof and at least one pharmaceutically acceptable excipient.

14. A pharmaceutical composition comprising an effective amount of a compound according to claim 8 or a pharmaceutically acceptable salt thereof and at least one pharmaceutically acceptable excipient.

15. A pharmaceutical composition comprising an effective amount of a compound according to claim 9 or a pharmaceutically acceptable salt thereof and at least one pharmaceutically acceptable excipient.

16. A pharmaceutical composition comprising an effective amount of a compound according to claim 15, or a pharmaceutically acceptable salt thereof and at least one pharmaceutically acceptable excipient.

17. A compound according to claim 1 wherein the crystallization or separation salts are formed from picric acid or oxalic acid.

18. A compound according to claim 1 wherein the pharmaceutically acceptable salts are the hydrochloride, hydrobromide, sulphate, hydrogen sulphate, dihydrogen phosphate, methanesulphonate, methyl sulphate, maleate, fumarate and 2-naphthalenesulphonate salts.

* * * * *